US008184822B2

(12) United States Patent
Carreras et al.

(10) Patent No.: US 8,184,822 B2
(45) Date of Patent: May 22, 2012

(54) ANR SIGNAL PROCESSING TOPOLOGY

(75) Inventors: Ricardo F. Carreras, Southborough, MA (US); Daniel M. Gauger, Jr., Cambridge, MA (US); Marcel Joho, Framingham, MA (US)

(73) Assignee: Bose Corporation, Framingham, MA (US)

( * ) Notice: Subject to any disclaimer, the term of this patent is extended or adjusted under 35 U.S.C. 154(b) by 380 days.

(21) Appl. No.: 12/430,984

(22) Filed: Apr. 28, 2009

(65) Prior Publication Data

US 2010/0272276 A1 Oct. 28, 2010

(51) Int. Cl.
*A61F 11/06* (2006.01)

(52) U.S. Cl. ...................................................... 381/71.6

(58) Field of Classification Search .................. 381/71.6
See application file for complete search history.

(56) References Cited

U.S. PATENT DOCUMENTS

| | | | | |
|---|---|---|---|---|
| 4,455,675 | A * | 6/1984 | Bose et al. | 381/74 |
| 5,018,202 | A * | 5/1991 | Takahashi et al. | 381/71.5 |
| 5,138,664 | A * | 8/1992 | Kimura et al. | 381/71.6 |
| 5,172,416 | A * | 12/1992 | Allie et al. | 381/71.11 |
| 5,202,927 | A | 4/1993 | Topholm | |
| 5,255,325 | A | 10/1993 | Ishimitsu et al. | |
| 5,303,306 | A | 4/1994 | Brillhart et al. | |
| 5,337,366 | A | 8/1994 | Eguchi et al. | |
| 5,388,062 | A | 2/1995 | Knutson | |
| 5,416,846 | A * | 5/1995 | Tamura et al. | 381/71.8 |
| 5,452,361 | A * | 9/1995 | Jones | 381/71.6 |
| 5,481,615 | A * | 1/1996 | Eatwell et al. | 381/71.6 |
| 5,699,436 | A | 12/1997 | Claybaugh et al. | |
| 5,710,819 | A | 1/1998 | Tøpholm et al. | |
| 5,724,433 | A | 3/1998 | Engebretson et al. | |
| 5,815,582 | A * | 9/1998 | Claybaugh et al. | 381/71.6 |
| 5,825,897 | A * | 10/1998 | Andrea et al. | 381/71.6 |
| 5,841,856 | A | 11/1998 | Ide | |
| 6,035,050 | A | 3/2000 | Weinfurtner et al. | |
| 6,041,126 | A * | 3/2000 | Terai et al. | 381/71.6 |
| 6,061,456 | A * | 5/2000 | Andrea et al. | 381/71.6 |
| 6,094,489 | A | 7/2000 | Ishige et al. | |
| 6,118,878 | A * | 9/2000 | Jones | 381/72 |

(Continued)

FOREIGN PATENT DOCUMENTS

DE 3733132 A1 4/1989

(Continued)

OTHER PUBLICATIONS

Invitation to Pay Additional Fees dated Jul. 26, 2010 for PCT/2010/032486.

(Continued)

*Primary Examiner* — Elvin G Enad
*Assistant Examiner* — Robert W Horn
(74) *Attorney, Agent, or Firm* — Bose Corporation

(57) ABSTRACT

An ANR circuit, possibly of a personal ANR device, incorporates an signal processing topology to support the provision of feedback-based ANR, feedforward-based ANR and pass-through audio in which the topology incorporates a branch in which feedback anti-noise sounds are generated from feedback reference sounds received from a feedback microphone, a branch in which feedforward anti-noise sounds are generated from feedforward reference sounds, and a branch in which modified pass-through audio sounds are generated from pass-through audio sounds received from an audio source, wherein these three branches are combined to combine the generated sounds of each branch into a single output by which an acoustic driver, possibly of the personal ANR device, is driven.

16 Claims, 18 Drawing Sheets

U.S. PATENT DOCUMENTS

| | | | | |
|---|---|---|---|---|
| 6,160,893 | A | 12/2000 | Saunders et al. | |
| 6,236,731 | B1 | 5/2001 | Brennan et al. | |
| 6,418,228 | B1 | 7/2002 | Terai et al. | |
| 6,522,753 | B1 | 2/2003 | Matsuzawa et al. | |
| 6,567,524 | B1 | 5/2003 | Svean et al. | |
| 6,717,537 | B1 | 4/2004 | Fang et al. | |
| 6,741,707 | B2 * | 5/2004 | Ray et al. | 381/71.11 |
| 6,744,882 | B1 | 6/2004 | Gupta et al. | |
| 6,829,365 | B1 * | 12/2004 | Kim | 381/370 |
| 6,870,940 | B2 | 3/2005 | Meyer et al. | |
| 6,937,738 | B2 * | 8/2005 | Armstrong et al. | 381/312 |
| 6,993,140 | B1 * | 1/2006 | Chen | 381/71.6 |
| 6,996,241 | B2 * | 2/2006 | Ray et al. | 381/71.11 |
| 7,039,195 | B1 | 5/2006 | Svean et al. | |
| 7,215,766 | B2 * | 5/2007 | Wurtz | 379/430 |
| 7,216,139 | B2 | 5/2007 | Langhammer et al. | |
| 7,248,705 | B1 * | 7/2007 | Mishan | 381/71.6 |
| 7,251,335 | B1 * | 7/2007 | Chen | 381/71.6 |
| 7,260,209 | B2 | 8/2007 | Harvey et al. | |
| 7,277,722 | B2 * | 10/2007 | Rosenzweig | 455/550.1 |
| 7,292,973 | B1 | 11/2007 | Johnston et al. | |
| 7,317,802 | B2 * | 1/2008 | Wurtz | 381/71.6 |
| 7,433,481 | B2 * | 10/2008 | Armstrong et al. | 381/312 |
| 7,627,127 | B2 | 12/2009 | Aida et al. | |
| 7,706,550 | B2 | 4/2010 | Amada et al. | |
| 7,813,515 | B2 | 10/2010 | Botti et al. | |
| 7,813,520 | B2 * | 10/2010 | Von Dach et al. | 381/372 |
| 7,822,210 | B2 | 10/2010 | Barnhill | |
| 7,853,028 | B2 | 12/2010 | Fischer | |
| 7,885,422 | B2 | 2/2011 | Sinai | |
| 7,920,903 | B2 | 4/2011 | Ueda et al. | |
| 7,933,420 | B2 | 4/2011 | Copley et al. | |
| 7,945,065 | B2 | 5/2011 | Menzl et al. | |
| 7,983,908 | B2 | 7/2011 | Kuboki et al. | |
| 2001/0039190 | A1 | 11/2001 | Bhatnagar | |
| 2003/0021429 | A1 | 1/2003 | Ratcliff et al. | |
| 2003/0053636 | A1 * | 3/2003 | Goldberg et al. | 381/71.11 |
| 2003/0228019 | A1 * | 12/2003 | Eichler et al. | 381/71.8 |
| 2004/0138769 | A1 | 7/2004 | Akiho | |
| 2004/0240677 | A1 | 12/2004 | Onishi et al. | |
| 2005/0025323 | A1 | 2/2005 | Botti et al. | |
| 2005/0069146 | A1 * | 3/2005 | Bum | 381/74 |
| 2005/0078845 | A1 | 4/2005 | Aschoff et al. | |
| 2005/0117754 | A1 | 6/2005 | Sakawaki | |
| 2006/0088171 | A1 * | 4/2006 | Yeh | 381/74 |
| 2007/0003078 | A1 | 1/2007 | Escott et al. | |
| 2007/0076896 | A1 | 4/2007 | Hosaka et al. | |
| 2007/0223715 | A1 | 9/2007 | Barath et al. | |
| 2007/0250314 | A1 | 10/2007 | Kuboki et al. | |
| 2007/0253569 | A1 * | 11/2007 | Bose | 381/71.6 |
| 2008/0025530 | A1 | 1/2008 | Romesburg | |
| 2008/0037801 | A1 * | 2/2008 | Alves et al. | 381/71.6 |
| 2008/0095383 | A1 | 4/2008 | Pan et al. | |
| 2008/0162072 | A1 | 7/2008 | Copley et al. | |
| 2008/0165981 | A1 * | 7/2008 | Wurtz | 381/71.6 |
| 2008/0192957 | A1 | 8/2008 | Kubo | |
| 2008/0207123 | A1 | 8/2008 | Andersen | |
| 2008/0292113 | A1 | 11/2008 | Tian | |
| 2008/0310652 | A1 | 12/2008 | Gustavsson | |
| 2009/0034748 | A1 | 2/2009 | Sibbald | |
| 2009/0034768 | A1 | 2/2009 | Lunner | |
| 2009/0103750 | A1 | 4/2009 | Chilakapati et al. | |
| 2009/0161889 | A1 | 6/2009 | Magrath | |
| 2010/0166203 | A1 * | 7/2010 | Peissig et al. | 381/71.6 |
| 2010/0254550 | A1 | 10/2010 | Martin et al. | |
| 2010/0260362 | A1 | 10/2010 | Sander et al. | |
| 2010/0266136 | A1 * | 10/2010 | Kelloniemi et al. | 381/71.6 |
| 2010/0266137 | A1 | 10/2010 | Sibbald et al. | |
| 2010/0272275 | A1 | 10/2010 | Carreras et al. | |
| 2010/0272276 | A1 * | 10/2010 | Carreras et al. | 381/71.6 |
| 2010/0272277 | A1 | 10/2010 | Joho et al. | |
| 2010/0272278 | A1 | 10/2010 | Joho et al. | |
| 2010/0272279 | A1 | 10/2010 | Joho et al. | |
| 2010/0272280 | A1 | 10/2010 | Joho et al. | |
| 2010/0272281 | A1 | 10/2010 | Carreras et al. | |
| 2010/0272282 | A1 | 10/2010 | Carreras | |
| 2010/0272283 | A1 | 10/2010 | Carreras et al. | |
| 2010/0272284 | A1 | 10/2010 | Joho et al. | |
| 2010/0274564 | A1 | 10/2010 | Bakalos et al. | |
| 2010/0310086 | A1 | 12/2010 | Magrath et al. | |
| 2010/0322432 | A1 | 12/2010 | Clemow | |
| 2011/0130176 | A1 | 6/2011 | Magrath et al. | |
| 2011/0188665 | A1 | 8/2011 | Burge et al. | |

FOREIGN PATENT DOCUMENTS

| | | | |
|---|---|---|---|
| JP | 2254898 | A | 10/1990 |
| JP | 5341792 | A | 12/1993 |
| JP | 8006571 | A | 1/1996 |
| JP | 2005257720 | A | 9/2005 |
| WO | 2005112849 | A2 | 12/2005 |
| WO | 2009041012 | A1 | 4/2009 |

OTHER PUBLICATIONS

International Search Report and Written Opinion dated Oct. 1, 2010 for PCT/2010/032486.

Invitation to Pay Additional Fees dated Aug. 3, 2010 for PCT/US2010/032557.

International Search Report and Written Opinion dated Sep. 16, 2010 for PCT/US10/032557.

* cited by examiner

ANR SIGNAL PROCESSING TOPOLOGY

TECHNICAL FIELD

This disclosure relates to personal active noise reduction (ANR) devices to reduce acoustic noise in the vicinity of at least one of a user's ears.

BACKGROUND

Headphones and other physical configurations of personal ANR device worn about the ears of a user for purposes of isolating the user's ears from unwanted environmental sounds have become commonplace. In particular, ANR headphones in which unwanted environmental noise sounds are countered with the active generation of anti-noise sounds, have become highly prevalent, even in comparison to headphones or ear plugs employing only passive noise reduction (PNR) technology, in which a user's ears are simply physically isolated from environmental noises. Especially of interest to users are ANR headphones that also incorporate audio listening functionality, thereby enabling a user to listen to electronically provided audio (e.g., playback of recorded audio or audio received from another device) without the intrusion of unwanted environmental noise sounds.

Unfortunately, despite various improvements made over time, existing personal ANR devices continue to suffer from a variety of drawbacks. Foremost among those drawbacks are undesirably high rates of power consumption leading to short battery life, undesirably narrow ranges of audible frequencies in which unwanted environmental noise sounds are countered through ANR, instances of unpleasant ANR-originated sounds, and instances of actually creating more unwanted noise sounds than whatever unwanted environmental sounds may be reduced.

SUMMARY

An ANR circuit, possibly of a personal ANR device, incorporates an signal processing topology to support the provision of feedback-based ANR, feedforward-based ANR and pass-through audio in which the topology incorporates a branch in which feedback anti-noise sounds are generated from feedback reference sounds received from a feedback microphone, a branch in which feedforward anti-noise sounds are generated from feedforward reference sounds, and a branch in which modified pass-through audio sounds are generated from pass-through audio sounds received from an audio source, wherein these three branches are combined to combine the generated sounds of each branch into a single output by which an acoustic driver, possibly of the personal ANR device, is driven.

In one aspect, a personal ANR device includes a first earpiece; a first feedback microphone disposed within the first earpiece; a first feedforward microphone disposed on an external portion of the personal ANR device; a first acoustic driver disposed within the first earpiece; and a first ANR circuit. The ANR circuit is structured to receive a first feedback reference signal from the first feedback microphone; generate first feedback anti-noise sounds from digital data representing at least the first feedback reference signal; receive a first feedforward reference signal from the first feedforward microphone; generate first feedforward anti-noise sounds from digital data representing at least the first feedforward reference signal; receive a pass-through audio signal from an audio source; generate first modified pass-through audio sounds from digital data representing at least the pass-through audio signal; and output a first output signal conveying the first feedback anti-noise sounds, the first feedforward anti-noise sounds and the first modified pass-through audio sounds to be acoustically output by the first acoustic driver.

Implementations may include, and are not limited to, one or more of the following features. The personal ANR device may further include a second earpiece; a second feedback microphone disposed within the second earpiece; and a second acoustic driver disposed within the first earpiece. The first ANR circuit may be further structured to: receive a second feedback reference signal from the second feedback microphone; generate second feedback anti-noise sounds from digital data representing at least the second feedback reference signal; generate second feedforward anti-noise sounds from digital data representing at least the first feedforward reference signal; generate second modified pass-through audio sounds from digital data representing at least the pass-through audio signal; and output a second output signal conveying the second feedback anti-noise sounds, the second feedforward anti-noise sounds and the second modified pass-through audio sounds to be acoustically output by the second acoustic driver. The personal ANR device may further include the audio source, and the audio source may be an audio playback device or a communications microphone.

The personal ANR may further include a second feedforward microphone disposed on an external portion of the personal ANR device, and the first ANR circuit may be further structured to: receive a second feedback reference signal from the second feedback microphone; generate second feedback anti-noise sounds from digital data representing at least the second feedback reference signal; receive a second feedforward reference signal from the second feedforward microphone; generate second feedforward anti-noise sounds from digital data representing at least the second feedforward reference signal; generate second modified pass-through audio sounds from digital data representing at least the pass-through audio signal; and output a second output signal conveying the second feedback anti-noise sounds, the second feedforward anti-noise sounds and the second modified pass-through audio sounds to be acoustically output by the second acoustic driver. The personal ANR device may further include a second feedforward microphone disposed on an external portion of the personal ANR device; and a second ANR circuit that may be structured to: receive a second feedback reference signal from the second feedback microphone; generate second feedback anti-noise sounds from digital data representing at least the second feedback reference signal; receive a second feedforward reference signal from the second feedforward microphone; generate second feedforward anti-noise sounds from digital data representing at least the second feedforward reference signal; receive the pass-through audio signal from the audio source; generate second modified pass-through audio sounds from digital data representing at least the pass-through audio signal; and output a second signal conveying the second feedback anti-noise sounds, the second feedforward anti-noise sounds and the second modified pass-through audio sounds to be acoustically output by the second acoustic driver.

In one aspect, an ANR circuit includes a signal processing topology having a feedback ANR pathway, a feedforward ANR pathway, and a pass-through audio pathway, wherein the ANR circuit is structured to: receive a feedback reference signal from a feedback microphone; generate feedback anti-noise sounds in the feedback ANR pathway from digital data representing at least the feedback reference signal; receive a feedforward reference signal from a feedforward microphone; generate feedforward anti-noise sounds in the feedforward ANR pathway from digital data representing at least the feedforward reference signal; receive a pass-through audio signal from an audio source; generate modified pass-through audio sounds in the pass-through audio pathway from digital data representing the pass-through audio signal; combine the feedback anti-noise sounds from the feedback ANR pathway, the feedforward anti-noise sounds from the feedforward ANR pathway, and the modified pass-through audio sounds from the pass-through audio pathway; and output an output signal conveying a combination of the feedback anti-noise sounds, the feedforward anti-noise sounds and the modified pass-through audio sounds to be acoustically output by an acoustic driver.

Implementations may include, and are not limited to, one or more of the following features. The ANR circuit may be further structured to enable one or both of the points at which the feedforward anti-noise sounds or modified pass-through audio sounds are combined with feedback anti-noise sounds to be selectable, possibly between a point along the feedback pathway preceding a block of filters employed to generate the feedback anti-noise sounds, and a point along the feedback pathway following that block of filters. Further, the pass-through audio pathway may include a block of filters to at least split the modified pass-through audio sounds into higher frequency sounds and lower frequency sounds at a selectable crossover frequency, and to route the lower and higher frequency sounds to different ones of the locations along the feedback pathway with a selectable crossover frequency possibly being selected to route the entirety of the modified pass-through audio sounds to one or the other of those locations.

The ANR circuit may further include a compression controller monitoring the output signal, and one or more VGAs operable by the compression controller to reduce an amplitude of one or both of the feedback anti-noise sounds and the feedforward anti-noise sounds in response to the compression controller detecting an indication of impending clipping in the first output signal, wherein the point at which the modified pass-through audio sounds are combined with feedback anti-noise sounds may be selectable between a point along the feedback pathway preceding a VGA positioned along the feedback pathway, and a point following that VGA.

Other features and advantages of the invention will be apparent from the description and claims that follow.

DETAILED DESCRIPTION

What is disclosed and what is claimed herein is intended to be applicable to a wide variety of personal ANR devices, i.e., devices that are structured to be at least partly worn by a user in the vicinity of at least one of the user's ears to provide ANR functionality for at least that one ear. It should be noted that although various specific implementations of personal ANR devices, such as headphones, two-way communications headsets, earphones, earbuds, wireless headsets (also known as "earsets") and ear protectors are presented with some degree of detail, such presentations of specific implementations are intended to facilitate understanding through the use of examples, and should not be taken as limiting either the scope of disclosure or the scope of claim coverage.

It is intended that what is disclosed and what is claimed herein is applicable to personal ANR devices that provide two-way audio communications, one-way audio communications (i.e., acoustic output of audio electronically provided by another device), or no communications, at all. It is intended that what is disclosed and what is claimed herein is applicable to personal ANR devices that are wirelessly connected to other devices, that are connected to other devices through electrically and/or optically conductive cabling, or that are not connected to any other device, at all. It is intended that what is disclosed and what is claimed herein is applicable to personal ANR devices having physical configurations structured to be worn in the vicinity of either one or both ears of a user, including and not limited to, headphones with either one or two earpieces, over-the-head headphones, behind-the-neck headphones, headsets with communications microphones (e.g., boom microphones), wireless headsets (i.e., earsets), single earphones or pairs of earphones, as well as hats or helmets incorporating one or two earpieces to enable audio communications and/or ear protection. Still other physical configurations of personal ANR devices to which what is disclosed and what is claimed herein are applicable will be apparent to those skilled in the art.

Beyond personal ANR devices, what is disclosed and claimed herein is also meant to be applicable to the provision of ANR in relatively small spaces in which a person may sit or stand, including and not limited to, phone booths, car passenger cabins, etc.

Figure 1:
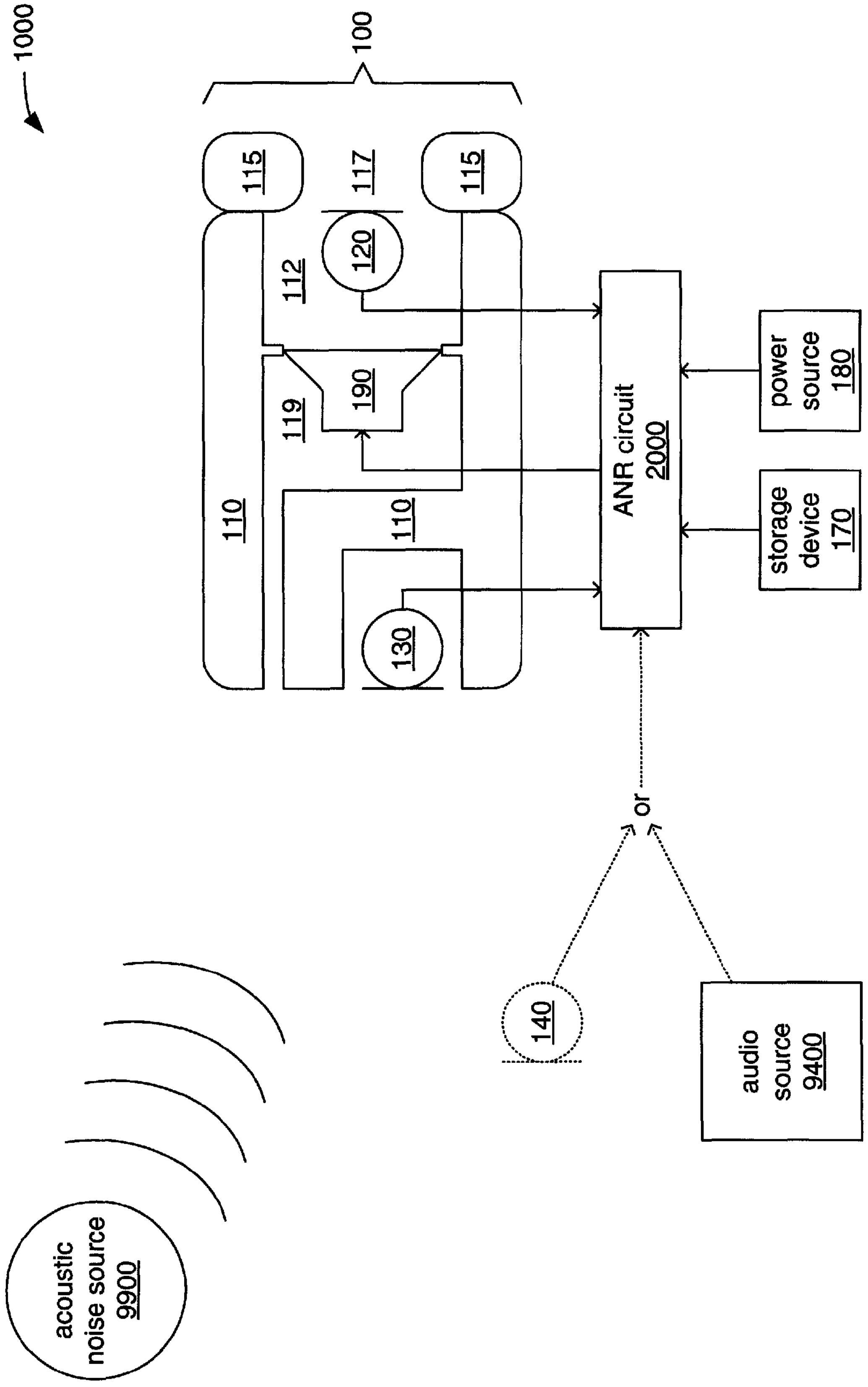
FIG. 1 is a block diagram of portions of an implementation of a personal ANR device.
Figure 2B:
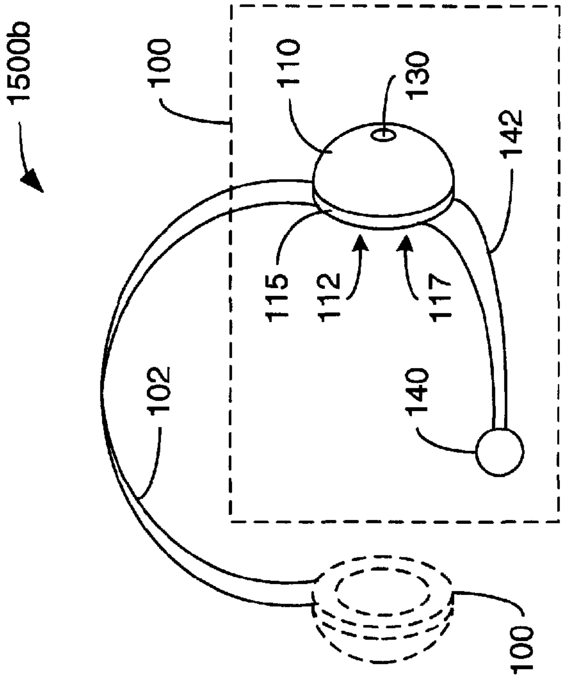
FIGS. 2*a* through 2*f* depict possible physical configurations of the personal ANR device of FIG. 1.

FIG. 1 provides a block diagram of a personal ANR device 1000 structured to be worn by a user to provide active noise reduction (ANR) in the vicinity of at least one of the user's ears. As will also be explained in greater detail, the personal ANR device 1000 may have any of a number of physical configurations, some possible ones of which are depicted in FIGS. 2*a* through 2*f*. Some of these depicted physical configurations incorporate a single earpiece 100 to provide ANR to only one of the user's ears, and others incorporate a pair of earpieces 100 to provide ANR to both of the user's ears. However, it should be noted that for the sake of simplicity of discussion, only a single earpiece 100 is depicted and described in relation to FIG. 1. As will also be explained in greater detail, the personal ANR device 1000 incorporates at least one ANR circuit 2000 that may provide either or both of feedback-based ANR and feedforward-based ANR, in addition to possibly further providing pass-through audio. FIGS. 3*a* and 3*b* depict a couple of possible internal architectures of the ANR circuit 2000 that are at least partly dynamically configurable. Further, FIGS. 4*a* through 4*e* depict some possible signal processing topologies and FIGS. 5*a* through 5*e* depict some possible filter block topologies that may the ANR circuit 2000 may be dynamically configured to adopt. Further, the provision of either or both of feedback-based ANR and feedforward-based ANR is in addition to at least some degree of passive noise reduction (PNR) provided by the structure of each earpiece 100. Still further, FIGS. 6*a* through 6*c* depict various forms of triple-buffering that may be employed in dynamically configuring signal processing topologies, filter block topologies and/or still other ANR settings.

Each earpiece 100 incorporates a casing 110 having a cavity 112 at least partly defined by the casing 110 and by at least a portion of an acoustic driver 190 disposed within the casing to acoustically output sounds to a user's ear. This manner of positioning the acoustic driver 190 also partly defines another cavity 119 within the casing 110 that is separated from the cavity 112 by the acoustic driver 190. The casing 110 carries an ear coupling 115 surrounding an opening to the cavity 112 and having a passage 117 that is formed through the ear coupling 115 and that communicates with the opening to the cavity 112. In some implementations, an acoustically transparent screen, grill or other form of perforated panel (not shown) may be positioned in or near the passage 117 in a manner that obscures the cavity and/or the passage 117 from view for aesthetic reasons and/or to protect components within the casing 110 from damage. At times when the earpiece 100 is worn by a user in the vicinity of one of the user's ears, the passage 117 acoustically couples the cavity 112 to the ear canal of that ear, while the ear coupling 115 engages portions of the ear to form at least some degree of acoustic seal therebetween. This acoustic seal enables the casing 110, the ear coupling 115 and portions of the user's head surrounding the ear canal (including portions of the ear) to cooperate to acoustically isolate the cavity 112, the passage 117 and the ear canal from the environment external to the casing 110 and the user's head to at least some degree, thereby providing some degree of PNR.

In some variations, the cavity 119 may be coupled to the environment external to the casing 110 via one or more acoustic ports (only one of which is shown), each tuned by their dimensions to a selected range of audible frequencies to enhance characteristics of the acoustic output of sounds by the acoustic driver 190 in a manner readily recognizable to those skilled in the art. Also, in some variations, one or more tuned ports (not shown) may couple the cavities 112 and 119, and/or may couple the cavity 112 to the environment external to the casing 110. Although not specifically depicted, screens, grills or other forms of perforated or fibrous structures may be positioned within one or more of such ports to prevent passage of debris or other contaminants therethrough and/or to provide a selected degree of acoustic resistance therethrough.

In implementations providing feedforward-based ANR, a feedforward microphone 130 is disposed on the exterior of the casing 110 (or on some other portion of the personal ANR device 1000) in a manner that is acoustically accessible to the environment external to the casing 110. This external positioning of the feedforward microphone 130 enables the feedforward microphone 130 to detect environmental noise sounds, such as those emitted by an acoustic noise source 9900, in the environment external to the casing 110 without the effects of any form of PNR or ANR provided by the personal ANR device 1000. As those familiar with feedforward-based ANR will readily recognize, these sounds detected by the feedforward microphone 130 are used as a reference from which feedforward anti-noise sounds are derived and then acoustically output into the cavity 112 by the acoustic driver 190. The derivation of the feedforward anti-noise sounds takes into account the characteristics of the PNR provided by the personal ANR device 1000, characteristics and position of the acoustic driver 190 relative to the feedforward microphone 130, and/or acoustic characteristics of the cavity 112 and/or the passage 117. The feedforward anti-noise sounds are acoustically output by the acoustic driver 190 with amplitudes and time shifts calculated to acoustically interact with the noise sounds of the acoustic noise source 9900 that are able to enter into the cavity 112, the passage 117 and/or an ear canal in a subtractive manner that at least attenuates them.

In implementations providing feedback-based ANR, a feedback microphone 120 is disposed within the cavity 112. The feedback microphone 120 is positioned in close proximity to the opening of the cavity 112 and/or the passage 117 so as to be positioned close to the entrance of an ear canal when the earpiece 100 is worn by a user. The sounds detected by the feedback microphone 120 are used as a reference from which feedback anti-noise sounds are derived and then acoustically output into the cavity 112 by the acoustic driver 190. The derivation of the feedback anti-noise sounds takes into account the characteristics and position of the acoustic driver 190 relative to the feedback microphone 120, and/or the acoustic characteristics of the cavity 112 and/or the passage 117, as well as considerations that enhance stability in the provision of feedback-based ANR. The feedback anti-noise sounds are acoustically output by the acoustic driver 190 with amplitudes and time shifts calculated to acoustically interact with noise sounds of the acoustic noise source 9900 that are able to enter into the cavity 112, the passage 117 and/or the ear canal (and that have not been attenuated by whatever PNR) in a subtractive manner that at least attenuates them.

The personal ANR device 1000 further incorporates one of the ANR circuit 2000 associated with each earpiece 100 of the personal ANR device 1000 such that there is a one-to-one correspondence of ANR circuits 2000 to earpieces 100. Either a portion of or substantially all of each ANR circuit 2000 may be disposed within the casing 110 of its associated earpiece 100. Alternatively and/or additionally, a portion of or substantially all of each ANR circuit 2000 may be disposed within another portion of the personal ANR device 1000. Depending on whether one or both of feedback-based ANR and feedforward-based ANR are provided in an earpiece 100 associated with the ANR circuit 2000, the ANR circuit 2000 is coupled to one or both of the feedback microphone 120 and the feedforward microphone 130, respectively. The ANR circuit 2000 is further coupled to the acoustic driver 190 to cause the acoustic output of anti-noise sounds.

In some implementations providing pass-through audio, the ANR circuit 2000 is also coupled to an audio source 9400 to receive pass-through audio from the audio source 9400 to be acoustically output by the acoustic driver 190. The pass-through audio, unlike the noise sounds emitted by the acoustic noise source 9900, is audio that a user of the personal ANR device 1000 desires to hear. Indeed, the user may wear the personal ANR device 1000 to be able to hear the pass-through audio without the intrusion of the acoustic noise sounds. The pass-through audio may be a playback of recorded audio, transmitted audio, or any of a variety of other forms of audio that the user desires to hear. In some implementations, the audio source 9400 may be incorporated into the personal ANR device 1000, including and not limited to, an integrated audio playback component or an integrated audio receiver component. In other implementations, the personal ANR device 1000 incorporates a capability to be coupled either wirelessly or via an electrically or optically conductive cable to the audio source 9400 where the audio source 9400 is an entirely separate device from the personal ANR device 1000 (e.g., a CD player, a digital audio file player, a cell phone, etc.).

In other implementations pass-through audio is received from a communications microphone 140 integrated into variants of the personal ANR device 1000 employed in two-way communications in which the communications microphone

140 is positioned to detect speech sounds produced by the user of the personal ANR device 1000. In such implementations, an attenuated or otherwise modified form of the speech sounds produced by the user may be acoustically output to one or both ears of the user as a communications sidetone to enable the user to hear their own voice in a manner substantially similar to how they normally would hear their own voice when not wearing the personal ANR device 1000.

In support of the operation of at least the ANR circuit 2000, the personal ANR device 1000 may further incorporate one or both of a storage device 170, a power source 180 and/or a processing device (not shown). As will be explained in greater detail, the ANR circuit 2000 may access the storage device 170 (perhaps through a digital serial interface) to obtain ANR settings with which to configure feedback-based and/or feed-forward-based ANR. As will also be explained in greater detail, the power source 180 may be a power storage device of limited capacity (e.g., a battery).

FIGS. 2*a* through 2*f* depict various possible physical configurations that may be adopted by the personal ANR device 1000 of FIG. 1. As previously discussed, different implementations of the personal ANR device 1000 may have either one or two earpieces 100, and are structured to be worn on or near a user's head in a manner that enables each earpiece 100 to be positioned in the vicinity of a user's ear.

Figure 2A:
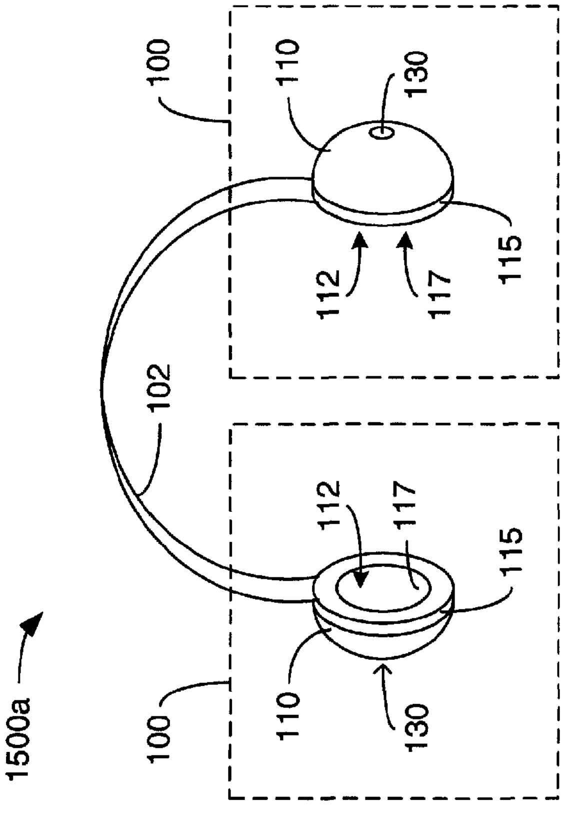
Figure 3A:
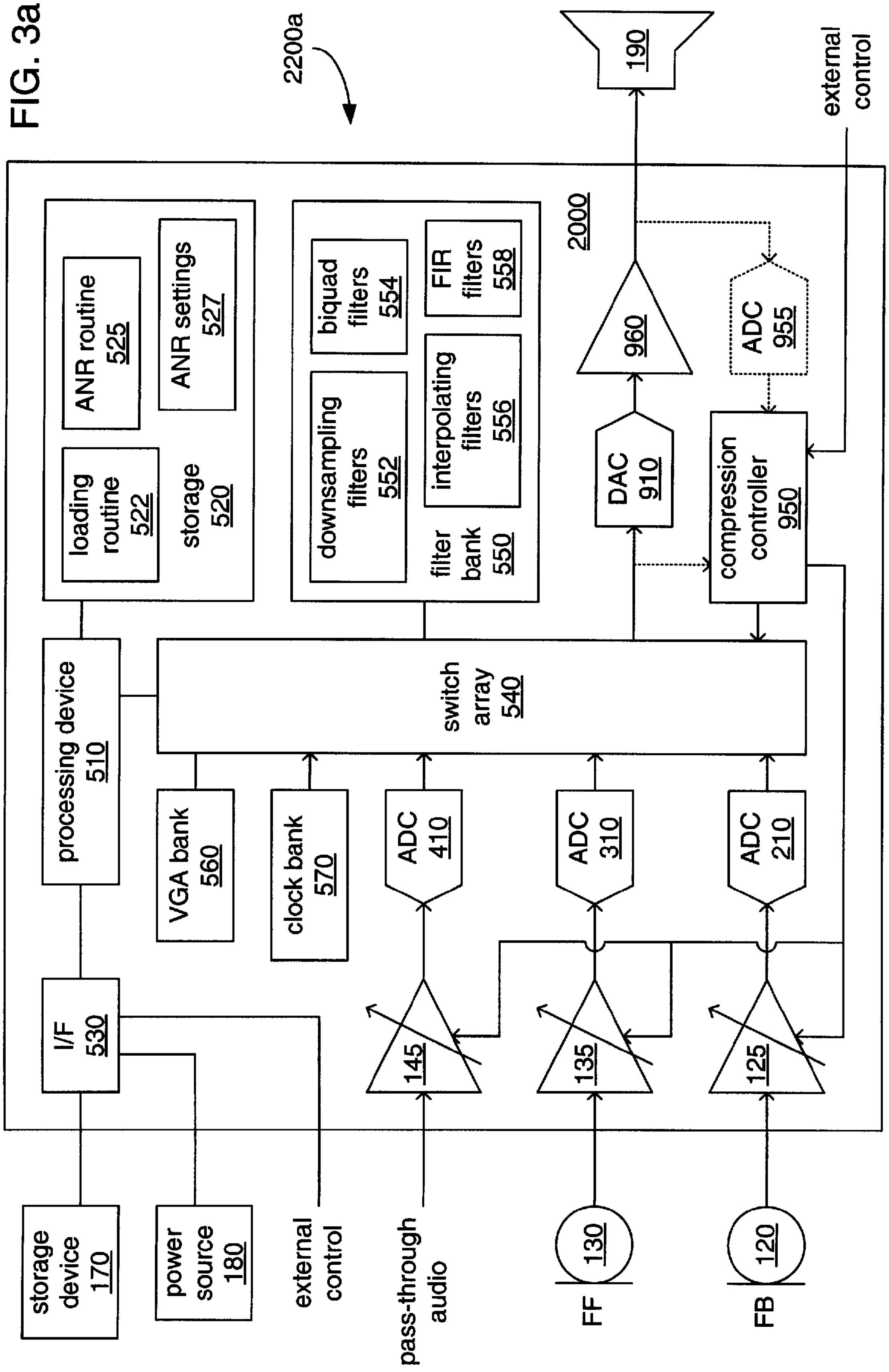
FIGS. 3*a* and 3*b* depict possible internal architectures of an ANR circuit of the personal ANR device of FIG. 1.
Figure 3B:
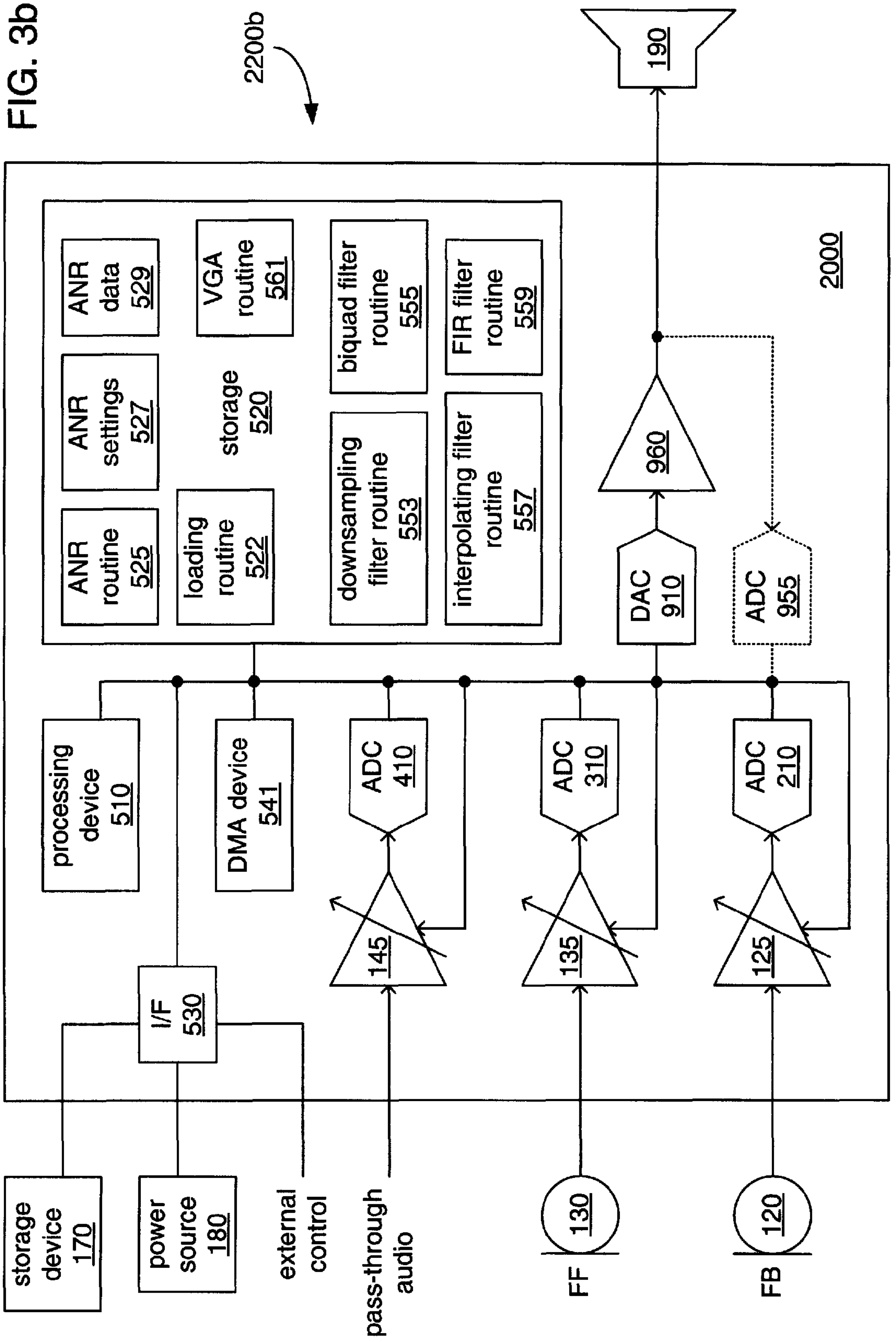

FIG. 2*a* depicts an "over-the-head" physical configuration 1500*a* of the personal ANR device 1000 that incorporates a pair of earpieces 100 that are each in the form of an earcup, and that are connected by a headband 102. However, and although not specifically depicted, an alternate variant of the physical configuration 1500*a* may incorporate only one of the earpieces 100 connected to the headband 102. Another alternate variant of the physical configuration 1500*a* may replace the headband 102 with a different band structured to be worn around the back of the head and/or the back of the neck of a user.

In the physical configuration 1500*a*, each of the earpieces 100 may be either an "on-ear" (also commonly called "supra-aural") or an "around-ear" (also commonly called "circum-aural") form of earcup, depending on their size relative to the pinna of a typical human ear. As previously discussed, each earpiece 100 has the casing 110 in which the cavity 112 is formed, and that 110 carries the ear coupling 115. In this physical configuration, the ear coupling 115 is in the form of a flexible cushion (possibly ring-shaped) that surrounds the periphery of the opening into the cavity 112 and that has the passage 117 formed therethrough that communicates with the cavity 112.

Where the earpieces 100 are structured to be worn as over-the-ear earcups, the casing 110 and the ear coupling 115 cooperate to substantially surround the pinna of an ear of a user. Thus, when such a variant of the personal ANR device 1000 is correctly worn, the headband 102 and the casing 110 cooperate to press the ear coupling 115 against portions of a side of the user's head surrounding the pinna of an ear such that the pinna is substantially hidden from view. Where the earpieces 100 are structured to be worn as on-ear earcups, the casing 110 and ear coupling 115 cooperate to overlie peripheral portions of a pinna that surround the entrance of an associated ear canal. Thus, when correctly worn, the headband 102 and the casing 110 cooperate to press the ear coupling 115 against portions of the pinna in a manner that likely leaves portions of the periphery of the pinna visible. The pressing of the flexible material of the ear coupling 115 against either portions of a pinna or portions of a side of a head surrounding a pinna serves both to acoustically couple the ear canal with the cavity 112 through the passage 117, and to form the previously discussed acoustic seal to enable the provision of PNR.

FIG. 2*b* depicts another over-the-head physical configuration 1500*b* that is substantially similar to the physical configuration 1500*a*, but in which one of the earpieces 100 additionally incorporates a communications microphone 140 connected to the casing 110 via a microphone boom 142. When this particular one of the earpieces 100 is correctly worn, the microphone boom 142 extends from the casing 110 and generally alongside a portion of a cheek of a user to position the communications microphone 140 closer to the mouth of the user to detect speech sounds acoustically output from the user's mouth. However, and although not specifically depicted, an alternative variant of the physical configuration 1500*b* is possible in which the communications microphone 140 is more directly disposed on the casing 110, and the microphone boom 142 is a hollow tube that opens on one end in the vicinity of the user's mouth and on the other end in the vicinity of the communications microphone 140 to convey sounds from the vicinity of the user's mouth to the vicinity of the communications microphone 140.

FIG. 2*b* also depicts the other of the earpieces 100 with broken lines to make clear that still another variant of the physical configuration 1500*b* of the personal ANR device 1000 is possible that incorporates only the one of the earpieces 100 that incorporates the microphone boom 142 and the communications microphone 140. In such another variant, the headband 102 would still be present and would continue to be worn over the head of the user.

Figure 2D:
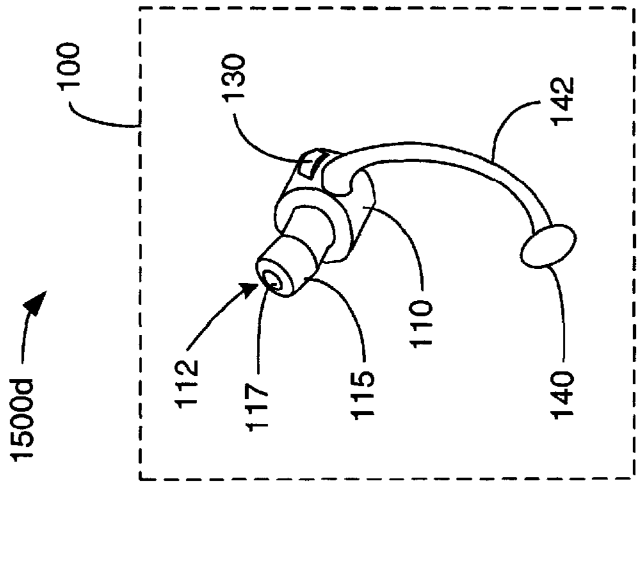
Figure 2C:
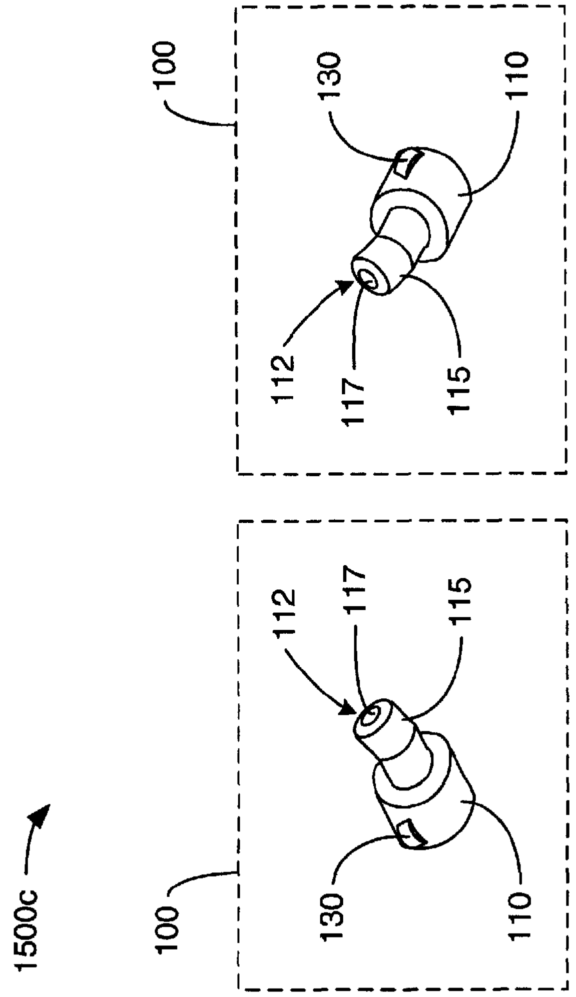

FIG. 2*c* depicts an "in-ear" (also commonly called "intra-aural") physical configuration 1500*c* of the personal ANR device 1000 that incorporates a pair of earpieces 100 that are each in the form of an in-ear earphone, and that may or may not be connected by a cord and/or by electrically or optically conductive cabling (not shown). However, and although not specifically depicted, an alternate variant of the physical configuration 1500*c* may incorporate only one of the earpieces 100.

As previously discussed, each of the earpieces 100 has the casing 110 in which the open cavity 112 is formed, and that carries the ear coupling 115. In this physical configuration, the ear coupling 115 is in the form of a substantially hollow tube-like shape defining the passage 117 that communicates with the cavity 112. In some implementations, the ear coupling 115 is formed of a material distinct from the casing 110 (possibly a material that is more flexible than that from which the casing 110 is formed), and in other implementations, the ear coupling 115 is formed integrally with the casing 110.

Portions of the casing 110 and/or of the ear coupling 115 cooperate to engage portions of the concha and/or the ear canal of a user's ear to enable the casing 110 to rest in the vicinity of the entrance of the ear canal in an orientation that acoustically couples the cavity 112 with the ear canal through the ear coupling 115. Thus, when the earpiece 100 is properly positioned, the entrance to the ear canal is substantially "plugged" to create the previously discussed acoustic seal to enable the provision of PNR.

FIG. 2*d* depicts another in-ear physical configuration 1500*d* of the personal ANR device 1000 that is substantially similar to the physical configuration 1500*c*, but in which one of the earpieces 100 is in the form of a single-ear headset (sometimes also called an "earset") that additionally incorporates a communications microphone 140 disposed on the casing 110. When this earpiece 100 is correctly worn, the communications microphone 140 is generally oriented towards the vicinity of the mouth of the user in a manner chosen to detect speech sounds produced by the user. However, and although not specifically depicted, an alternative variant of the physical configuration 1500*d* is possible in which sounds from the vicinity of the user's mouth are conveyed to the communications microphone 140 through a tube (not shown), or in which the communications microphone 140 is disposed on a boom (not shown) connected to the casing 110 and positioning the communications microphone 140 in the vicinity of the user's mouth.

Although not specifically depicted in FIG. 2*d*, the depicted earpiece 100 of the physical configuration 1500*d* having the communications microphone 140 may or may not be accompanied by another earpiece having the form of an in-ear earphone (such as one of the earpieces 100 depicted in FIG. 2*c*) that may or may not be connected to the earpiece 100 depicted in FIG. 2*d* via a cord or conductive cabling (also not shown).

Figure 2F:
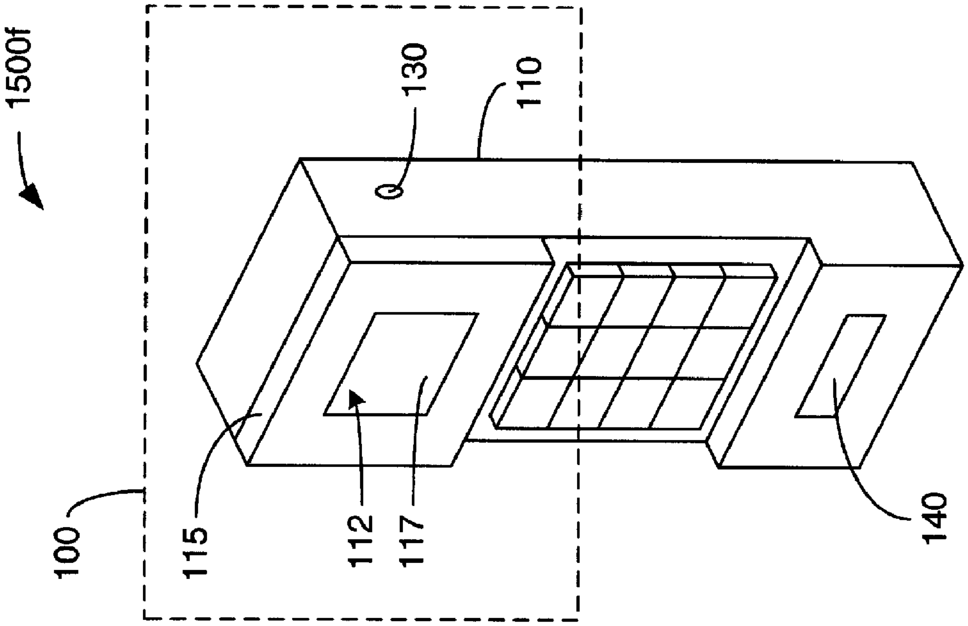
Figure 2E:
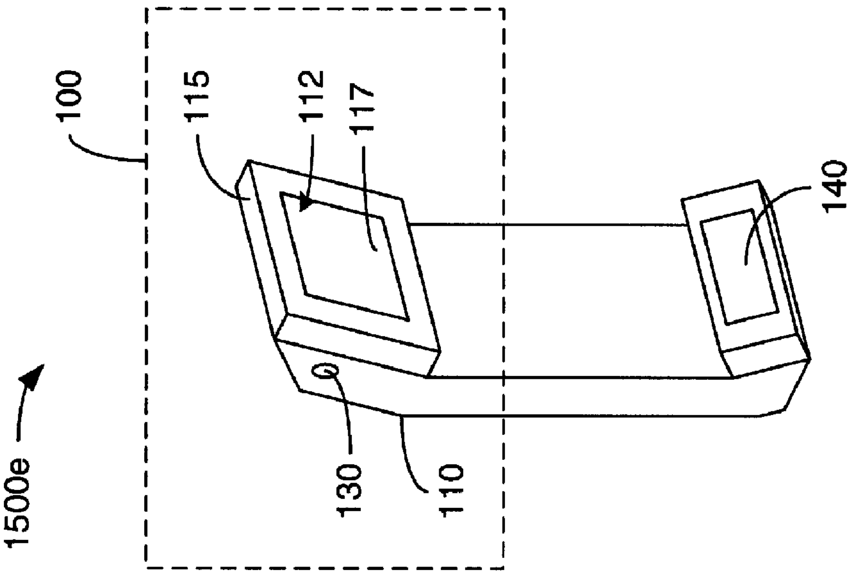

FIG. 2*e* depicts a two-way communications handset physical configuration 1500*e* of the personal ANR device 1000 that incorporates a single earpiece 100 that is integrally formed with the rest of the handset such that the casing 110 is the casing of the handset, and that may or may not be connected by conductive cabling (not shown) to a cradle base with which it may be paired. In a manner not unlike one of the earpieces 100 of an on-the-ear variant of either of the physical configurations 1500*a* and 1500*b*, the earpiece 100 of the physical configuration 1500*e* carries a form of the ear coupling 115 that is configured to be pressed against portions of the pinna of an ear to enable the passage 117 to acoustically couple the cavity 112 to an ear canal. In various possible implementations, ear coupling 115 may be formed of a material distinct from the casing 110, or may be formed integrally with the casing 110.

FIG. 2*f* depicts another two-way communications handset physical configuration 1500*f* of the personal ANR device 1000 that is substantially similar to the physical configuration 1500*e*, but in which the casing 110 is shaped somewhat more appropriately for portable wireless communications use, possibly incorporating user interface controls and/or display(s) to enable the dialing of phone numbers and/or the selection of radio frequency channels without the use of a cradle base.

FIGS. 3*a* and 3*b* depict possible internal architectures, either of which may be employed by the ANR circuit 2000 in implementations of the personal ANR device 1000 in which the ANR circuit 2000 is at least partially made up of dynamically configurable digital circuitry. In other words, the internal architectures of FIGS. 3*a* and 3*b* are dynamically configurable to adopt any of a wide variety of signal processing topologies and filter block topologies during operation of the ANR circuit 2000. FIGS. 4*a-g* depict various examples of signal processing topologies that may be adopted by the ANR circuit 2000 in this manner, and FIGS. 5*a-e* depict various examples of filter block topologies that may also be adopted by the ANR circuit 2000 for use within an adopted signal processing topology in this manner. However, and as those skilled in the art will readily recognize, other implementations of the personal ANR device 1000 are possible in which the ANR circuit 2000 is largely or entirely implemented with analog circuitry and/or digital circuitry lacking such dynamic configurability.

In implementations in which the circuitry of the ANR circuit 2000 is at least partially digital, analog signals representing sounds that are received or output by the ANR circuit 2000 may require conversion into or creation from digital data that also represents those sounds. More specifically, in both of the internal architectures 2200*a* and 2200*b*, analog signals received from the feedback microphone 120 and the feedforward microphone 130, as well as whatever analog signal representing pass-through audio may be received from either the audio source 9400 or the communications microphone 140, are digitized by analog-to-digital converters (ADCs) of the ANR circuit 2000. Also, whatever analog signal is provided to the acoustic driver 190 to cause the acoustic driver 190 to acoustically output anti-noise sounds and/or pass-through audio is created from digital data by a digital-to-analog converter (DAC) of the ANR circuit 2000. Further, either analog signals or digital data representing sounds may be manipulated to alter the amplitudes of those represented sounds by either analog or digital forms, respectively, of variable gain amplifiers (VGAs).

FIG. 3*a* depicts a possible internal architecture 2200*a* of the ANR circuit 2000 in which digital circuits that manipulate digital data representing sounds are selectively interconnected through one or more arrays of switching devices that enable those interconnections to be dynamically configured during operation of the ANR circuit 2000. Such a use of switching devices enables pathways for movement of digital data among various digital circuits to be defined through programming. More specifically, blocks of digital filters of varying quantities and/or types are able to be defined through which digital data associated with feedback-based ANR, feedforward-based ANR and pass-through audio are routed to perform these functions. In employing the internal architecture 2200*a*, the ANR circuit 2000 incorporates ADCs 210, 310 and 410; a processing device 510; a storage 520; an interface (I/F) 530; a switch array 540; a filter bank 550; and a DAC 910. Various possible variations may further incorporate one or more of analog VGAs 125, 135 and 145; a VGA bank 560; a clock bank 570; a compression controller 950; a further ADC 955; and/or an audio amplifier 960.

The ADC 210 receives an analog signal from the feedback microphone 120, the ADC 310 receives an analog signal from the feedforward microphone 130, and the ADC 410 receives an analog signal from either the audio source 9400 or the communications microphone 140. As will be explained in greater detail, one or more of the ADCs 210, 310 and 410 may receive their associated analog signals through one or more of the analog VGAs 125, 135 and 145, respectively. The digital outputs of each of the ADCs 210, 310 and 410 are coupled to the switch array 540. Each of the ADCs 210, 310 and 410 may be designed to employ a variant of the widely known sigma-delta analog-to-digital conversion algorithm for reasons of power conservation and inherent ability to reduce digital data representing audible noise sounds that might otherwise be introduced as a result of the conversion process. However, as those skilled in the art will readily recognize, any of a variety of other analog-to-digital conversion algorithms may be employed. Further, in some implementations, at least the ADC 410 may be bypassed and/or entirely dispensed with where at least the pass-through audio is provided to the ANR circuit 2000 as digital data, rather than as an analog signal.

The filter bank 550 incorporates multiple digital filters, each of which has its inputs and outputs coupled to the switch array 540. In some implementations, all of the digital filters within the filter bank 550 are of the same type, while in other implementations, the filter bank 550 incorporates a mixture of different types of digital filters. As depicted, the filter bank 550 incorporates a mixture of multiple downsampling filters 552, multiple biquadratic (biquad) filters 554, multiple interpolating filters 556, and multiple finite impulse response (FIR) filters 558, although other varieties of filters may be incorporated, as those skilled in the art will readily recognize. Further, among each of the different types of digital filters may be digital filters optimized to support different data transfer rates. By way of example, differing ones of the biquad filters 554 may employ coefficient values of differing bit-widths, or differing ones of the FIR filters 558 may have differing quantities of taps. The VGA bank 560 (if present) incorporates multiple digital VGAs, each of which has its inputs and outputs coupled to the switch array 540. Also, the DAC 910 has its digital input coupled to the switch array 540. The clock bank 570 (if present) provides multiple clock signal outputs coupled to the switch array 540 that simultaneously provide multiple clock signals for clocking data between components at selected data transfer rates and/or other purposes. In some implementations, at least a subset of the multiple clock signals are synchronized multiples of one another to simultaneously support different data transfer rates in different pathways in which the movement of data at those different data transfer rates in those different pathways is synchronized.

The switching devices of the switch array 540 are operable to selectively couple different ones of the digital outputs of the ADCs 210, 310 and 410; the inputs and outputs of the digital filters of the filter bank 550; the inputs and outputs of the digital VGAs of the VGA bank 560; and the digital input of the DAC 910 to form a set of interconnections therebetween that define a topology of pathways for the movement of digital data representing various sounds. The switching devices of the switch array 540 may also be operable to selectively couple different ones of the clock signal outputs of the clock bank 570 to different ones of the digital filters of the filter bank 550 and/or different ones of the digital VGAs of the VGA bank 560. It is largely in this way that the digital circuitry of the internal architecture 2200*a* is made dynamically configurable. In this way, varying quantities and types of digital filters and/or digital VGAs may be positioned at various points along different pathways defined for flows of digital data associated with feedback-based ANR, feedforward-based ANR and pass-through audio to modify sounds represented by the digital data and/or to derive new digital data representing new sounds in each of those pathways. Also, in this way, different data transfer rates may be selected by which digital data is clocked at different rates in each of the pathways.

In support of feedback-based ANR, feedforward-based ANR and/or pass-through audio, the coupling of the inputs and outputs of the digital filters within the filter bank 550 to the switch array 540 enables inputs and outputs of multiple digital filters to be coupled through the switch array 540 to create blocks of filters. As those skilled in the art will readily recognize, by combining multiple lower-order digital filters into a block of filters, multiple lower-order digital filters may be caused to cooperate to implement higher order functions without the use of a higher-order filter. Further, in implementations having a variety of types of digital filters, blocks of filters may be created that employ a mix of filters to perform a still greater variety of functions. By way of example, with the depicted variety of filters within the filter bank 550, a filter block (i.e., a block of filters) may be created having at least one of the downsampling filters 552, multiple ones of the biquad filters 554, at least one of the interpolating filters 556, and at least one of the FIR filters 558.

In some implementations, at least some of the switching devices of the switch array 540 may be implemented with binary logic devices enabling the switch array 540, itself, to be used to implement basic binary math operations to create summing nodes where pathways along which different pieces of digital data flow are brought together in a manner in which those different pieces of digital data are arithmetically summed, averaged, and/or otherwise combined. In such implementations, the switch array 540 may be based on a variant of dynamically programmable array of logic devices. Alternatively and/or additionally, a bank of binary logic devices or other form of arithmetic logic circuitry (not shown) may also be incorporated into the ANR circuit 2000 with the inputs and outputs of those binary logic devices and/or other form of arithmetic logic circuitry also being coupled to the switch array 540.

In the operation of switching devices of the switch array 540 to adopt a topology by creating pathways for the flow of data representing sounds, priority may be given to creating a pathway for the flow of digital data associated with feedback-based ANR that has as low a latency as possible through the switching devices. Also, priority may be given in selecting digital filters and VGAs that have as low a latency as possible from among those available in the filter bank 550 and the VGA bank 560, respectively. Further, coefficients and/or other settings provided to digital filters of the filter bank 550 that are employed in the pathway for digital data associated with feedback-based ANR may be adjusted in response to whatever latencies are incurred from the switching devices of the switch array 540 employed in defining the pathway. Such measures may be taken in recognition of the higher sensitivity of feedback-based ANR to the latencies of components employed in performing the function of deriving and/or acoustically outputting feedback anti-noise sounds. Although such latencies are also of concern in feedforward-based ANR, feedforward-based ANR is generally less sensitive to such latencies than feedback-based ANR. As a result, a degree of priority less than that given to feedback-based ANR, but greater than that given to pass-through audio, may be given to selecting digital filters and VGAs, and to creating a pathway for the flow of digital data associated with feedforward-based ANR.

The processing device 510 is coupled to the switch array 540, as well as to both the storage 520 and the interface 530. The processing device 510 may be any of a variety of types of processing device, including and not limited to, a general purpose central processing unit (CPU), a digital signal processor (DSP), a reduced instruction set computer (RISC) processor, a microcontroller, or a sequencer. The storage 520 may be based on any of a variety of data storage technologies, including and not limited to, dynamic random access memory (DRAM), static random access memory (SRAM), ferromagnetic disc storage, optical disc storage, or any of a variety of nonvolatile solid state storage technologies. Indeed, the storage 520 may incorporate both volatile and nonvolatile portions. Further, it will be recognized by those skilled in the art that although the storage 520 is depicted and discussed as if it were a single component, the storage 520 may be made up of multiple components, possibly including a combination of volatile and nonvolatile components. The interface 530 may support the coupling of the ANR circuit 2000 to one or more digital communications buses, including digital serial buses by which the storage device 170 (not to be confused with the storage 520) and/or other devices external to the ANR circuit 2000 (e.g., other processing devices, or other ANR circuits) may be coupled. Further, the interface 530 may provide one or more general purpose input/output (GPIO) electrical connections and/or analog electrical connections to support the coupling of manually-operable controls, indicator lights or other devices, such as a portion of the power source 180 providing an indication of available power.

In some implementations, the processing device 510 accesses the storage 520 to read a sequence of instructions of a loading routine 522, that when executed by the processing device 510, causes the processing device 510 to operate the interface 530 to access the storage device 170 to retrieve one or both of the ANR routine 525 and the ANR settings 527, and to store them in the storage 520. In other implementations, one or both of the ANR routine 525 and the ANR settings 527 are stored in a nonvolatile portion of the storage 520 such that they need not be retrieved from the storage device 170, even if power to the ANR circuit 2000 is lost.

Regardless of whether one or both of the ANR routine 525 and the ANR settings 527 are retrieved from the storage device 170, or not, the processing device 510 accesses the storage 520 to read a sequence of instructions of the ANR routine 525. The processing device 510 then executes that sequence of instructions, causing the processing device 510 to configure the switching devices of the switch array 540 to adopt a topology defining pathways for flows of digital data representing sounds and/or to provide differing clock signals to one or more digital filters and/or VGAs, as previously detailed. In some implementations, the processing device 510 is caused to configure the switching devices in a manner specified by a portion of the ANR settings 527, which the processing device 510 is also caused to read from the storage 520. Further, the processing device 510 is caused to set filter coefficients of various digital filters of the filter bank 550, gain settings of various VGAs of the VGA bank 560, and/or clock frequencies of the clock signal outputs of the clock bank 570 in a manner specified by a portion of the ANR settings 527.

In some implementations, the ANR settings 527 specify multiple sets of filter coefficients, gain settings, clock frequencies and/or configurations of the switching devices of the switch array 540, of which different sets are used in response to different situations. In other implementations, execution of sequences of instructions of the ANR routine 525 causes the processing device 510 to derive different sets of filter coefficients, gain settings, clock frequencies and/or switching device configurations in response to different situations. By way of example, the processing device 510 may be caused to operate the interface 530 to monitor a signal from the power source 180 that is indicative of the power available from the power source 180, and to dynamically switch between different sets of filter coefficients, gain settings, clock frequencies and/or switching device configurations in response to changes in the amount of available power.

By way of another example, the processing device 510 may be caused to monitor characteristics of sounds represented by digital data involved in feedback-based ANR, feedforward-based ANR and/or pass-through audio to determine whether or not it is desirable to alter the degree feedback-based and/or feedforward-based ANR provided. As will be familiar to those skilled in the art, while providing a high degree of ANR can be very desirable where there is considerable environmental noise to be attenuated, there can be other situations where the provision of a high degree of ANR can actually create a noisier or otherwise more unpleasant acoustic environment for a user of a personal ANR device than would the provision of less ANR. Therefore, the processing device 510 may be caused to alter the provision of ANR to adjust the degree of attenuation and/or the range of frequencies of environmental noise attenuated by the ANR provided in response to observed characteristics of one or more sounds. Further, as will also be familiar to those skilled in the art, where a reduction in the degree of attenuation and/or the range of frequencies is desired, it may be possible to simplify the quantity and/or type of filters used in implementing feedback-based and/or feedforward-based ANR, and the processing device 510 may be caused to dynamically switch between different sets of filter coefficients, gain settings, clock frequencies and/or switching device configurations to perform such simplifying, with the added benefit of a reduction in power consumption.

The DAC 910 is provided with digital data from the switch array 540 representing sounds to be acoustically output to an ear of a user of the personal ANR device 1000, and converts it to an analog signal representing those sounds. The audio amplifier 960 receives this analog signal from the DAC 910, and amplifies it sufficiently to drive the acoustic driver 190 to effect the acoustic output of those sounds.

The compression controller 950 (if present) monitors the sounds to be acoustically output for an indication of their amplitude being too high, indications of impending instances of clipping, actual instances of clipping, and/or other impending or actual instances of other audio artifacts. The compression controller 150 may either directly monitor digital data provided to the DAC 910 or the analog signal output by the audio amplifier 960 (through the ADC 955, if present). In response to such an indication, the compression controller 950 may alter gain settings of one or more of the analog VGAs 125, 135 and 145 (if present); and/or one or more of the VGAs of the VGA bank 560 placed in a pathway associated with one or more of the feedback-based ANR, feedforward-based ANR and pass-through audio functions to adjust amplitude, as will be explained in greater detail. Further, in some implementations, the compression controller 950 may also make such an adjustment in response to receiving an external control signal. Such an external signal may be provided by another component coupled to the ANR circuit 2000 to provide such an external control signal in response to detecting a condition such as an exceptionally loud environmental noise sound that may cause one or both of the feedback-based and feedforward-based ANR functions to react unpredictably.

FIG. 3*b* depicts another possible internal architecture 2200*b* of the ANR circuit 2000 in which a processing device accesses and executes stored machine-readable sequences of instructions that cause the processing device to manipulate digital data representing sounds in a manner that can be dynamically configured during operation of the ANR circuit 2000. Such a use of a processing device enables pathways for movement of digital data of a topology to be defined through programming. More specifically, digital filters of varying quantities and/or types are able to be defined and instantiated in which each type of digital filter is based on a sequence of instructions. In employing the internal architecture 2200*b*, the ANR circuit 2000 incorporates the ADCs 210, 310 and 410; the processing device 510; the storage 520; the interface 530; a direct memory access (DMA) device 540; and the DAC 910. Various possible variations may further incorporate one or more of the analog VGAs 125, 135 and 145; the ADC 955; and/or the audio amplifier 960. The processing device 510 is coupled directly or indirectly via one or more buses to the storage 520; the interface 530; the DMA device 540; the ADCs 210, 310 and 410; and the DAC 910 to at least enable the processing device 510 to control their operation. The processing device 510 may also be similarly coupled to one or more of the analog VGAs 125, 135 and 145 (if present); and to the ADC 955 (if present).

As in the internal architecture 2200*a*, the processing device 510 may be any of a variety of types of processing device, and once again, the storage 520 may be based on any of a variety of data storage technologies and may be made up of multiple components. Further, the interface 530 may support the coupling of the ANR circuit 2000 to one or more digital communications buses, and may provide one or more general purpose input/output (GPIO) electrical connections and/or analog electrical connections. The DMA device 540 may be based on a secondary processing device, discrete digital logic, a bus mastering sequencer, or any of a variety of other technologies.

Stored within the storage 520 are one or more of a loading routine 522, an ANR routine 525, ANR settings 527, ANR data 529, a downsampling filter routine 553, a biquad filter routine 555, an interpolating filter routine 557, a FIR filter routine 559, and a VGA routine 561. In some implementations, the processing device 510 accesses the storage 520 to read a sequence of instructions of the loading routine 522, that when executed by the processing device 510, causes the processing device 510 to operate the interface 530 to access the storage device 170 to retrieve one or more of the ANR routine 525, the ANR settings 527, the downsampling filter routine 553, the biquad filter routine 555, the interpolating filter routine 557, the FIR routine 559 and the VGA routine 561, and to store them in the storage 520. In other implementations, one or more of these are stored in a nonvolatile portion of the storage 520 such that they need not be retrieved from the storage device 170.

As was the case in the internal architecture 2200*a*, the ADC 210 receives an analog signal from the feedback microphone 120, the ADC 310 receives an analog signal from the feedforward microphone 130, and the ADC 410 receives an analog signal from either the audio source 9400 or the communications microphone 140 (unless the use of one or more of the ADCs 210, 310 and 410 is obviated through the direct receipt of digital data). Again, one or more of the ADCs 210, 310 and 410 may receive their associated analog signals through one or more of the analog VGAs 125, 135 and 145, respectively. As was also the case in the internal architecture 2200*a*, the DAC 910 converts digital data representing sounds to be acoustically output to an ear of a user of the personal ANR device 1000 into an analog signal, and the audio amplifier 960 amplifies this signal sufficiently to drive the acoustic driver 190 to effect the acoustic output of those sounds.

However, unlike the internal architecture 2200*a* where digital data representing sounds were routed via an array of switching devices, such digital data is stored in and retrieved from the storage 520. In some implementations, the processing device 510 repeatedly accesses the ADCs 210, 310 and 410 to retrieve digital data associated with the analog signals they receive for storage in the storage 520, and repeatedly retrieves the digital data associated with the analog signal output by the DAC 910 from the storage 520 and provides that digital data to the DAC 910 to enable the creation of that analog signal. In other implementations, the DMA device 540 (if present) transfers digital data among the ADCs 210, 310 and 410; the storage 520 and the DAC 910 independently of the processing device 510. In still other implementations, the ADCs 210, 310 and 410 and/or the DAC 910 incorporate "bus mastering" capabilities enabling each to write digital data to and/or read digital data from the storage 520 independently of the processing device 510. The ANR data 529 is made up of the digital data retrieved from the ADCs 210, 310 and 410, and the digital data provided to the DAC 910 by the processing device 510, the DMA device 540 and/or bus mastering functionality.

The downsampling filter routine 553, the biquad filter routine 555, the interpolating filter routine 557 and the FIR filter routine 559 are each made up of a sequence of instructions that cause the processing device 510 to perform a combination of calculations that define a downsampling filter, a biquad filter, an interpolating filter and a FIR filter, respectively. Further, among each of the different types of digital filters may be variants of those digital filters that are optimized for different data transfer rates, including and not limited to, differing bit widths of coefficients or differing quantities of taps. Similarly, the VGA routine 561 is made up of a sequence of instructions that cause the processing device 510 to perform a combination of calculations that define a VGA. Although not specifically depicted, a summing node routine may also be stored in the storage 520 made up of a sequence of instructions that similarly defines a summing node.

The ANR routine 525 is made up of a sequence of instructions that cause the processing device 510 to create a signal processing topology having pathways incorporating varying quantities of the digital filters and VGAs defined by the downsampling filter routine 553, the biquad filter routine 555, the interpolating filter routine 557, the FIR filter routine 559 and the VGA routine 561 to support feedback-based ANR, feedforward-based ANR and/or pass-through audio. The ANR routine 525 also causes the processing device 510 to perform the calculations defining each of the various filters and VGAs incorporated into that topology. Further, the ANR routine 525 either causes the processing device 510 to perform the moving of data among ADCs 210, 310 and 410, the storage 520 and the DAC 910, or causes the processing device 510 to coordinate the performance of such moving of data either by the DMA device 540 (if present) or by bus mastering operations performed by the ADCs 210, 310 and 410, and/or the DAC 910.

The ANR settings 527 is made up of data defining topology characteristics (including selections of digital filters), filter coefficients, gain settings, clock frequencies, data transfer rates and/or data sizes. In some implementations, the topology characteristics may also define the characteristics of any summing nodes to be incorporated into the topology. The processing device 510 is caused by the ANR routine 525 to employ such data taken from the ANR settings 527 in creating a signal processing topology (including selecting digital filters), setting the filter coefficients for each digital filter incorporated into the topology, and setting the gains for each VGA incorporated into the topology. The processing device 510 may be further caused by the ANR routine 525 to employ such data from the ANR settings 527 in setting clock frequencies and/or data transfer rates for the ADCs 210, 310 and 410; for the digital filters incorporated into the topology; for the VGAs incorporated into the topology; and for the DAC 910.

In some implementations, the ANR settings 527 specify multiple sets of topology characteristics, filter coefficients, gain settings, clock frequencies and/or data transfer rates, of which different sets are used in response to different situations. In other implementations, execution of sequences of instructions of the ANR routine 525 causes the processing device 510 to derive different sets of filter coefficients, gain settings, clock frequencies and/or data transfer rates for a given signal processing topology in different situations. By way of example, the processing device 510 may be caused to operate the interface 530 to monitor a signal from the power source 180 that is indicative of the power available from the power source 180, and to employ different sets of filter coefficients, gain settings, clock frequencies and/or data transfer rates in response to changes in the amount of available power.

By way of another example, the processing device 510 may be caused to alter the provision of ANR to adjust the degree of ANR required in response to observed characteristics of one or more sounds. Where a reduction in the degree of attenuation and/or the range of frequencies of noise sounds attenuated is possible and/or desired, it may be possible to simplify the quantity and/or type of filters used in implementing feedback-based and/or feedforward-based ANR, and the processing device 510 may be caused to dynamically switch between different sets of filter coefficients, gain settings, clock frequencies and/or data transfer rates to perform such simplifying, with the added benefit of a reduction in power consumption.

Therefore, in executing sequences of instructions of the ANR routine 525, the processing device 510 is caused to retrieve data from the ANR settings 527 in preparation for adopting a signal processing topology defining the pathways to be employed by the processing device 510 in providing feedback-based ANR, feedforward-based ANR and pass-through audio. The processing device 510 is caused to instantiate multiple instances of digital filters, VGAs and/or summing nodes, employing filter coefficients, gain settings and/or other data from the ANR settings 527. The processing device 510 is then further caused to perform the calculations defining each of those instances of digital filters, VGAs and summing nodes; to move digital data among those instances of digital filters, VGAs and summing nodes; and to at least coordinate the moving of digital data among the ADCs 210, 310 and 410, the storage 520 and the DAC 910 in a manner that conforms to the data retrieved from the ANR settings 527. At a subsequent time, the ANR routine 525 may cause the processing device 510 to change the signal processing topology, a digital filter, filter coefficients, gain settings, clock frequencies and/or data transfer rates during operation of the personal ANR device 1000. It is largely in this way that the digital circuitry of the internal architecture 2200*b* is made dynamically configurable. Also, in this way, varying quantities and types of digital filters and/or digital VGAs may be positioned at various points along a pathway of a topology defined for a flow of digital data to modify sounds represented by that digital data and/or to derive new digital data representing new sounds, as will be explained in greater detail.

In some implementations, the ANR routine 525 may cause the processing device 510 to give priority to operating the ADC 210 and performing the calculations of the digital filters, VGAs and/or summing nodes positioned along the pathway defined for the flow of digital data associated with feedback-based ANR. Such a measure may be taken in recognition of the higher sensitivity of feedback-based ANR to the latency between the detection of feedback reference sounds and the acoustic output of feedback anti-noise sounds.

The processing device 510 may be further caused by the ANR routine 525 to monitor the sounds to be acoustically output for indications of the amplitude being too high, clipping, indications of clipping about to occur, and/or other audio artifacts actually occurring or indications of being about to occur. The processing device 510 may be caused to either directly monitor digital data provided to the DAC 910 or the analog signal output by the audio amplifier 960 (through the ADC 955) for such indications. In response to such an indication, the processing device 510 may be caused to operate one or more of the analog VGAs 125, 135 and 145 to adjust at least one amplitude of an analog signal, and/or may be caused to operate one or more of the VGAs based on the VGA routine 561 and positioned within a pathway of a topology to adjust the amplitude of at least one sound represented by digital data, as will be explained in greater detail.

FIGS. 4*a* through 4*g* depict some possible signal processing topologies that may be adopted by the ANR circuit 2000 of the personal ANR device 1000 of FIG. 1. As previously discussed, some implementations of the personal ANR device 1000 may employ a variant of the ANR circuit 2000 that is at least partially programmable such that the ANR circuit 2000 is able to be dynamically configured to adopt different signal processing topologies during operation of the ANR circuit 2000. Alternatively, other implementations of the personal ANR device 1000 may incorporate a variant of the ANR circuit 2000 that is substantially inalterably structured to adopt one unchanging signal processing topology.

As previously discussed, separate ones of the ANR circuit 2000 are associated with each earpiece 100, and therefore, implementations of the personal ANR device 1000 having a pair of the earpieces 100 also incorporate a pair of the ANR circuits 2000. However, as those skilled in the art will readily recognize, other electronic components incorporated into the personal ANR device 1000 in support of a pair of the ANR circuits 2000, such as the power source 180, may not be duplicated. For the sake of simplicity of discussion and understanding, signal processing topologies for only a single ANR circuit 2000 are presented and discussed in relation to FIGS. 4*a*-*g*.

As also previously discussed, different implementations of the personal ANR device 1000 may provide only one of either feedback-based ANR or feedforward-based ANR, or may provide both. Further, different implementations may or may not additionally provide pass-through audio. Therefore, although signal processing topologies implementing all three of feedback-based ANR, feedforward-based ANR and pass-through audio are depicted in FIGS. 4*a*-*g*, it is to be understood that variants of each of these signal processing topologies are possible in which only one or the other of these two forms of ANR is provided, and/or in which pass-through audio is not provided. In implementations in which the ANR circuit 2000 is at least partially programmable, which of these two forms of ANR are provided and/or whether or not both forms of ANR are provided may be dynamically selectable during operation of the ANR circuit 2000.

Figure 4A:
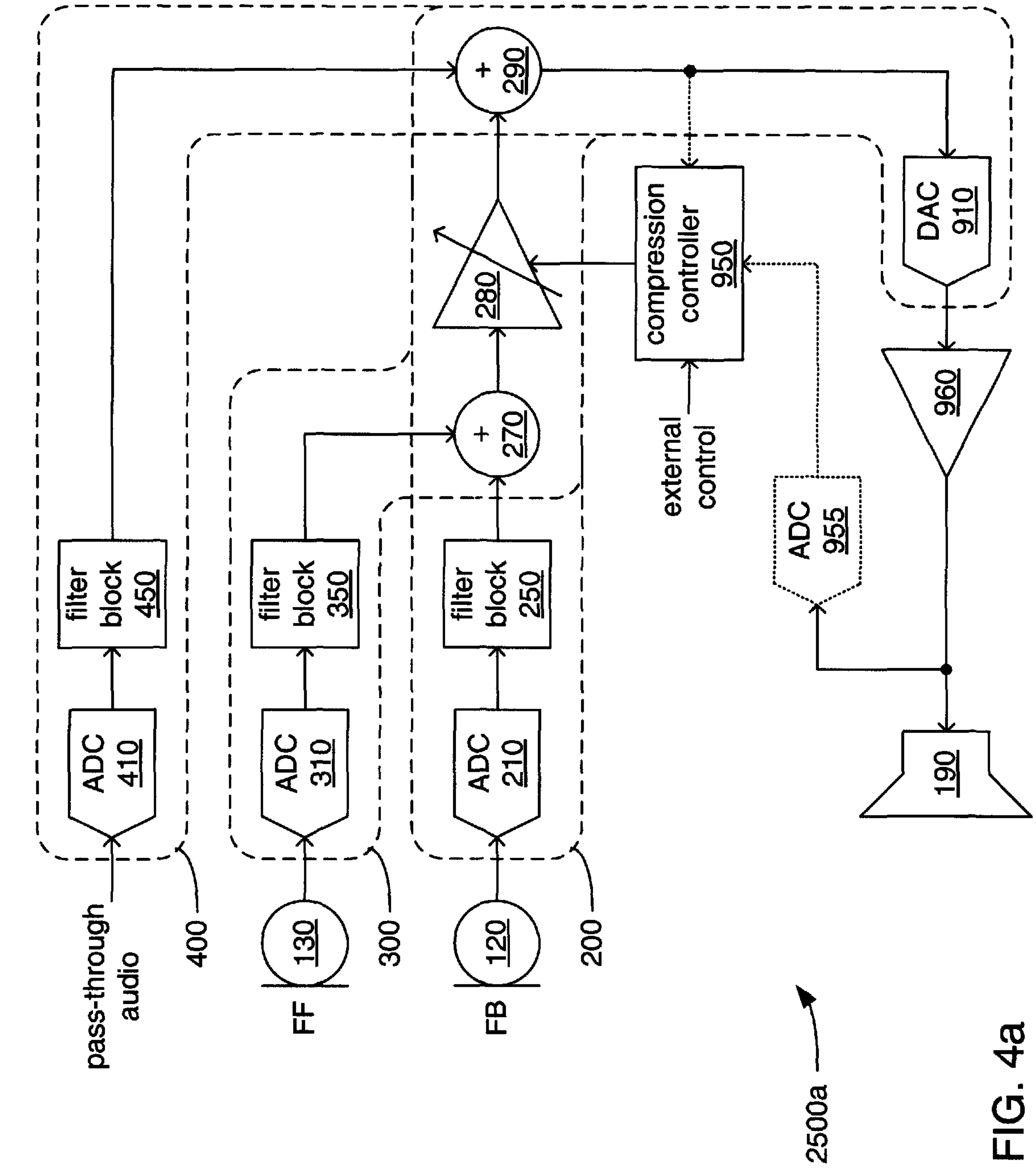
FIGS. 4*a* through 4*g* depict possible signal processing topologies that may be adopted by the ANR circuit of the personal ANR device of FIG. 1.

FIG. 4*a* depicts a possible signal processing topology 2500*a* for which the ANR circuit 2000 may be structured and/or programmed. Where the ANR circuit 2000 adopts the signal processing topology 2500*a*, the ANR circuit 2000 incorporates at least the DAC 910, the compression controller 950, and the audio amplifier 960. Depending, in part on whether one or both of feedback-based and feedforward-based ANR are supported, the ANR circuit 2000 further incorporates one or more of the ADCs 210, 310, 410 and/or 955; filter blocks 250, 350 and/or 450; and/or summing nodes 270 and/or 290.

Where the provision of feedback-based ANR is supported, the ADC 210 receives an analog signal from the feedback microphone 120 representing feedback reference sounds detected by the feedback microphone 120. The ADC 210 digitizes the analog signal from the feedback microphone 120, and provides feedback reference data corresponding to the analog signal output by the feedback microphone 120 to the filter block 250. One or more digital filters within the filter block 250 are employed to modify the data from the ADC 210 to derive feedback anti-noise data representing feedback anti-noise sounds. The filter block 250 provides the feedback anti-noise data to the VGA 280, possibly through the summing node 270 where feedforward-based ANR is also supported.

Where the provision of feedforward-based ANR is also supported, the ADC 310 receives an analog signal from the feedforward microphone 130, digitizes it, and provides feedforward reference data corresponding to the analog signal output by the feedforward microphone 130 to the filter block 350. One or more digital filters within the filter block 350 are employed to modify the feedforward reference data received from the ADC 310 to derive feedforward anti-noise data representing feedforward anti-noise sounds. The filter block 350 provides the feedforward anti-noise data to the VGA 280, possibly through the summing node 270 where feedback-based ANR is also supported.

At the VGA 280, the amplitude of one or both of the feedback and feedforward anti-noise sounds represented by the data received by the VGA 280 (either through the summing node 270, or not) may be altered under the control of the compression controller 950. The VGA 280 outputs its data (with or without amplitude alteration) to the DAC 910, possibly through the summing nodes 290 where talk-through audio is also supported.

In some implementations where pass-through audio is supported, the ADC 410 digitizes an analog signal representing pass-through audio received from the audio source 9400, the communications microphone 140 or another source and provides the digitized result to the filter block 450. In other implementations where pass-through audio is supported, the audio source 9400, the communications microphone 140 or another source provides digital data representing pass-through audio to the filter block 450 without need of analog-to-digital conversion. One or more digital filters within the filter block 450 are employed to modify the digital data representing the pass-through audio to derive a modified variant of the pass-through audio data in which the pass-through audio may be re-equalized and/or enhanced in other ways. The filter block 450 provides the pass-through audio data to the summing node 290 where the pass-through audio data is combined with the data being provided by the VGA 280 to the DAC 910.

The analog signal output by the DAC 910 is provided to the audio amplifier 960 to be amplified sufficiently to drive the acoustic driver 190 to acoustically output one or more of feedback anti-noise sounds, feedforward anti-noise sounds and pass-through audio. The compression controller 950 controls the gain of the VGA 280 to enable the amplitude of sound represented by data output by one or both of the filter blocks 250 and 350 to be reduced in response to indications of impending instances of clipping, actual occurrences of clipping and/or other undesirable audio artifacts being detected by the compression controller 950. The compression controller 950 may either monitor the data being provided to the DAC 910 by the summing node 290, or may monitor the analog signal output of the audio amplifier 960 through the ADC 955.

As further depicted in FIG. 4*a*, the signal processing topology 2500*a* defines multiple pathways along which digital data associated with feedback-based ANR, feedforward-based ANR and pass-through audio flow. Where feedback-based ANR is supported, the flow of feedback reference data and feedback anti-noise data among at least the ADC 210, the filter block 250, the VGA 280 and the DAC 910 defines a feedback-based ANR pathway 200. Similarly, where feedforward-based ANR is supported, the flow of feedforward reference data and feedforward anti-noise data among at least the ADC 310, the filter block 350, the VGA 280 and the DAC 910 defines a feedforward-based ANR pathway 300. Further, where pass-through audio is supported, the flow of pass-through audio data and modified pass-through audio data among at least the ADC 410, the filter block 450, the summing node 290 and the DAC 910 defines a pass-through audio pathway 400. Where both feedback-based and feedforward-based ANR are supported, the pathways 200 and 300 both further incorporate the summing node 270. Further, where pass-through audio is also supported, the pathways 200 and/or 300 incorporate the summing node 290.

In some implementations, digital data representing sounds may be clocked through all of the pathways 200, 300 and 400 that are present at the same data transfer rate. Thus, where the pathways 200 and 300 are combined at the summing node 270, and/or where the pathway 400 is combined with one or both of the pathways 200 and 300 at the summing node 400, all digital data is clocked through at a common data transfer rate, and that common data transfer rate may be set by a common synchronous data transfer clock. However, as is known to those skilled in the art and as previously discussed, the feedforward-based ANR and pass-through audio functions are less sensitive to latencies than the feedback-based ANR function. Further, the feedforward-based ANR and pass-through audio functions are more easily implemented with sufficiently high quality of sound with lower data sampling rates than the feedback-based ANR function. Therefore, in other implementations, portions of the pathways 300 and/or 400 may be operated at slower data transfer rates than the pathway 200. Preferably, the data transfer rates of each of the pathways 200, 300 and 400 are selected such that the pathway 200 operates with a data transfer rate that is an integer multiple of the data transfer rates selected for the portions of the pathways 300 and/or 400 that are operated at slower data transfer rates.

By way of example in an implementation in which all three of the pathways 200, 300 and 400 are present, the pathway 200 is operated at a data transfer rate selected to provide sufficiently low latency to enable sufficiently high quality of feedback-based ANR that the provision of ANR is not unduly compromised (e.g., by having anti-noise sounds out-of-phase with the noise sounds they are meant to attenuate, or instances of negative noise reduction such that more noise is actually being generated than attenuated, etc.), and/or sufficiently high quality of sound in the provision of at least the feedback anti-noise sounds. Meanwhile, the portion of the pathway 300 from the ADC 310 to the summing node 270 and the portion of the pathway 400 from the ADC 410 to the summing node 290 are both operated at lower data transfer rates (either the same lower data transfer rates or different ones) that still also enable sufficiently high quality of feedforward-based ANR in the pathway 300, and sufficiently high quality of sound in the provision of the feedforward anti-noise through the pathway 300 and/or pass-through audio through the pathway 400.

In recognition of the likelihood that the pass-through audio function may be even more tolerant of a greater latency and a lower sampling rate than the feedforward-based ANR function, the data transfer rate employed in that portion of the pathway 400 may be still lower than the data transfer rate of that portion of the pathway 300. To support such differences in transfer rates in one variation, one or both of the summing nodes 270 and 290 may incorporate sample-and-hold, buffering or other appropriate functionality to enable the combining of digital data received by the summing nodes 270 and 290 at different data transfer rates. This may entail the provision of two different data transfer clocks to each of the summing nodes 270 and 290. Alternatively, to support such differences in transfer rates in another variation, one or both of the filter blocks 350 and 450 may incorporate an upsampling capability (perhaps through the inclusion of an interpolating filter or other variety of filter incorporating an upsampling capability) to increase the data transfer rate at which the filter blocks 350 and 450 provide digital data to the summing nodes 270 and 290, respectively, to match the data transfer rate at which the filter block 250 provides digital data to the summing node 270, and subsequently, to the summing node 290.

It may be that in some implementations, multiple power modes may be supported in which the data transfer rates of the pathways 300 and 400 are dynamically altered in response to the availability of power from the power source 180 and/or in response to changing ANR requirements. More specifically, the data transfer rates of one or both of the pathway 300 and 400 up to the points where they are combined with the pathway 200 may be reduced in response to an indication of diminishing power being available from the power supply 180 and/or in response to the processing device 510 detecting characteristics in sounds represented by digital data indicating that the degree of attenuation and/or range of frequencies of noise sounds attenuated by the ANR provided can be reduced. In making determinations of whether or not such reductions in data transfer rates are possible, the processing device 510 may be caused to evaluate the effects of such reductions in data transfer rates on quality of sound through one or more of the pathways 200, 300 and 400, and/or the quality of feedback-based and/or feed-forward based ANR provided.

Figure 4B:
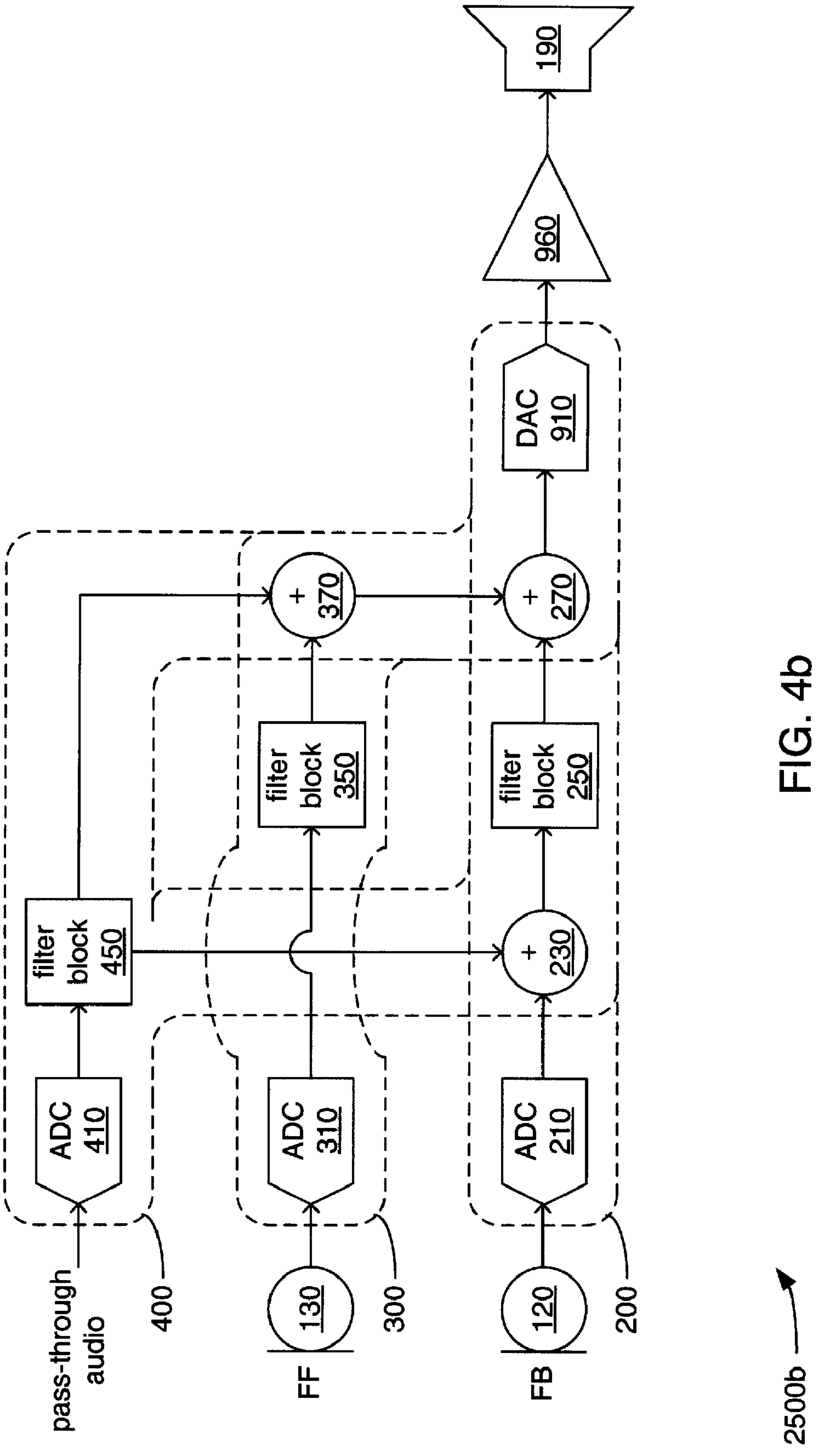

FIG. 4*b* depicts a possible signal processing topology 2500*b* for which the ANR circuit 2000 may be structured and/or programmed. Where the ANR circuit 2000 adopts the signal processing topology 2500*b*, the ANR circuit 2000 incorporates at least the DAC 910, the audio amplifier 960, the ADC 210, a pair of summing nodes 230 and 270, and a pair of filter blocks 250 and 450. The ANR circuit 2000 may further incorporate one or more of the ADC 410, the ADC 310, a filter block 350 and a summing node 370.

The ADC 210 receives and digitizes an analog signal from the feedback microphone 120 representing feedback reference sounds detected by the feedback microphone 120, and provides corresponding feedback reference data to the summing node 230. In some implementations, the ADC 410 digitizes an analog signal representing pass-through audio received from the audio source 9400, the communications microphone 140 or another source and provides the digitized result to the filter block 450. In other implementations, the audio source 9400, the communications microphone 140 or another source provides digital data representing pass-through audio to the filter block 450 without need of analog-to-digital conversion. One or more digital filters within the filter block 450 are employed to modify the digital data representing the pass-through audio to derive a modified variant of the pass-through audio data in which the pass-through audio may be re-equalized and/or enhanced in other ways. One or more digital filters within the filter block 450 also function as a crossover that divides the modified pass-through audio data into higher and lower frequency sounds, with data representing the higher frequency sounds being output to the summing node 270, and data representing the lower frequency sounds being output to the summing node 230. In various implementations, the crossover frequency employed in the filter block 450 is dynamically selectable during operation of the ANR circuit 2000, and may be selected to effectively disable the crossover function to cause data representing all frequencies of the modified pass-through audio to be output to either of the summing nodes 230 or 270. In this way, the point at which the modified pass-through audio data is combined with data for the feedback ANR function within the signal processing topology 2500*a* can be made selectable.

As just discussed, feedback reference data from the ADC 210 may be combined with data from the filter block 450 for the pass-through audio function (either the lower frequency sounds, or all of the modified pass-through audio) at the summing node 230. The summing node 230 outputs the possibly combined data to the filter block 250. One or more digital filters within the filter block 250 are employed to modify the data from summing node 230 to derive modified data representing at least feedback anti-noise sounds and possibly further-modified pass-through audio sounds. The filter block 250 provides the modified data to the summing node 270. The summing node 270 combines the data from the filter block 450 that possibly represents higher frequency sounds of the modified pass-through audio with the modified data from the filter block 250, and provides the result to the DAC 910 to create an analog signal. The provision of data by the filter block 450 to the summing node 270 may be through the summing node 370 where the provision of feedforward-based ANR is also supported.

Where the crossover frequency employed in the filter block 450 is dynamically selectable, various characteristics of the filters making up the filter block 450 may also be dynamically configurable. By way of example, the number and/or type of digital filters making up the filter block 450 may be dynamically alterable, as well as the coefficients for each of those digital filters. Such dynamic configurability may be deemed desirable to correctly accommodate changes among having no data from the filter block 450 being combined with feedback reference data from the ADC 210, having data from the filter block 450 representing lower frequency sounds being combined with feedback reference data from the ADC 210, and having data representing all of the modified pass-through audio from the filter block 450 being combined with feedback reference data from the ADC 210.

Where the provision of feedforward-based ANR is also supported, the ADC 310 receives an analog signal from the feedforward microphone 130, digitizes it, and provides feedforward reference data corresponding to the analog signal output by the feedforward microphone 130 to the filter block 350. One or more digital filters within the filter block 350 are employed to modify the feedforward reference data received from the ADC 310 to derive feedforward anti-noise data representing feedforward anti-noise sounds. The filter block 350 provides the feedforward anti-noise data to the summing node 370 where the feedforward anti-noise data is possibly combined with data that may be provided by the filter block 450 (either the higher frequency sounds, or all of the modified pass-through audio).

The analog signal output by the DAC 910 is provided to the audio amplifier 960 to be amplified sufficiently to drive the acoustic driver 190 to acoustically output one or more of feedback anti-noise sounds, feedforward anti-noise sounds and pass-through audio.

As further depicted in FIG. 4*b*, the signal processing topology 2500*b* defines its own variations of the pathways 200, 300 and 400 along which digital data associated with feedback-based ANR, feedforward-based ANR and pass-through audio, respectively, flow. In a manner not unlike the pathway 200 of the signal processing topology 2500*a*, the flow of feedback reference data and feedback anti-noise data among the ADC 210, the summing nodes 230 and 270, the filter block 250 and the DAC 910 defines the feedback-based ANR pathway 200 of the signal processing topology 2500*b*. Where feedforward-based ANR is supported, in a manner not unlike the pathway 300 of the signal processing topology 2500*a*, the flow of feedforward reference data and feedforward anti-noise data among the ADC 310, the filter block 350, the summing nodes 270 and 370, and the DAC 910 defines the feedforward-based ANR pathway 300 of the signal processing topology 2500*b*. However, in a manner very much unlike the pathway 400 of the signal processing topology 2500*a*, the ability of the filter block 450 of the signal processing topology 2500*b* to split the modified pass-through audio data into higher frequency and lower frequency sounds results in the pathway 400 of the signal processing topology 2500*b* being partially split. More specifically, the flow of digital data from the ADC 410 to the filter block 450 is split at the filter block 450. One split portion of the pathway 400 continues to the summing node 230, where it is combined with the pathway 200, before continuing through the filter block 250 and the summing node 270, and ending at the DAC 910. The other split portion of the pathway 400 continues to the summing node 370 (if present), where it is combined with the pathway 300 (if present), before continuing through the summing node 270 and ending at the DAC 910.

Also not unlike the pathways 200, 300 and 400 of the signal processing topology 2500*a*, the pathways 200, 300 and 400 of the signal processing topology 2500*b* may be operated with different data transfer rates. However, differences in data transfer rates between the pathway 400 and both of the pathways 200 and 300 would have to be addressed. Sample-and-hold, buffering or other functionality may be incorporated into each of the summing nodes 230, 270 and/or 370. Alternatively and/or additionally, the filter block 350 may incorporate interpolation or other upsampling capability in providing digital data to the summing node 370, and/or the filter block 450 may incorporate a similar capability in providing digital data to each of the summing nodes 230 and 370 (or 270, if the pathway 300 is not present).

Figure 4C:
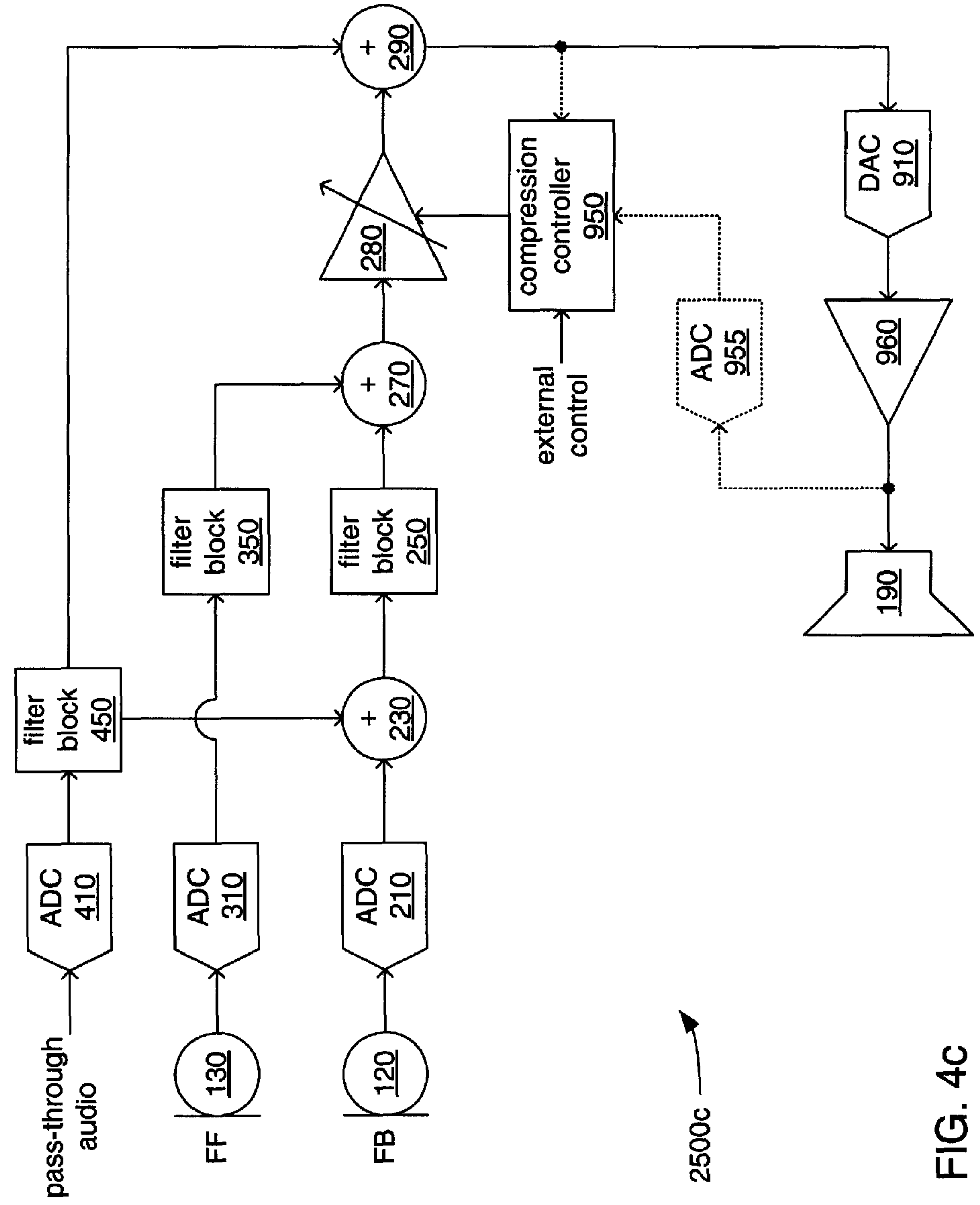

FIG. 4*c* depicts another possible signal processing topology 2500*c* for which the ANR circuit 2000 may be structured and/or programmed. Where the ANR circuit 2000 adopts the signal processing topology 2500*c*, the ANR circuit 2000 incorporates at least the DAC 910, the audio amplifier 960, the ADC 210, the summing node 230, the filter blocks 250 and 450, the VGA 280, another summing node 290, and the compressor 950. The ANR circuit 2000 may further incorporate one or more of the ADC 410, the ADC 310, the filter block 350, the summing node 270, and the ADC 955. The signal processing topologies 2500*b* and 2500*c* are similar in numerous ways. However, a substantial difference between the signal processing topologies 2500*b* and 2500*c* is the addition of the compressor 950 in the signal processing topology 2500*c* to enable the amplitudes of the sounds represented by data output by both of the filter blocks 250 and 350 to be reduced in response to the compressor 950 detecting actual instances or indications of impending instances of clipping and/or other undesirable audio artifacts.

The filter block 250 provides its modified data to the VGA 280 where the amplitude of the sounds represented by the data provided to the VGA 280 may be altered under the control of the compression controller 950. The VGA 280 outputs its data (with or without amplitude alteration) to the summing node 290, where it may be combined with data that may be output by the filter block 450 (perhaps the higher frequency sounds of the modified pass-through audio, or perhaps the entirety of the modified pass-through audio). In turn, the summing node 290 provides its output data to the DAC 910. Where the provision of feedforward-based ANR is also supported, the data output by the filter block 250 to the VGA 280 is routed through the summing node 270, where it is combined with the data output by the filter block 350 representing feedforward anti-noise sounds, and this combined data is provided to the VGA 280.

Figure 4D:
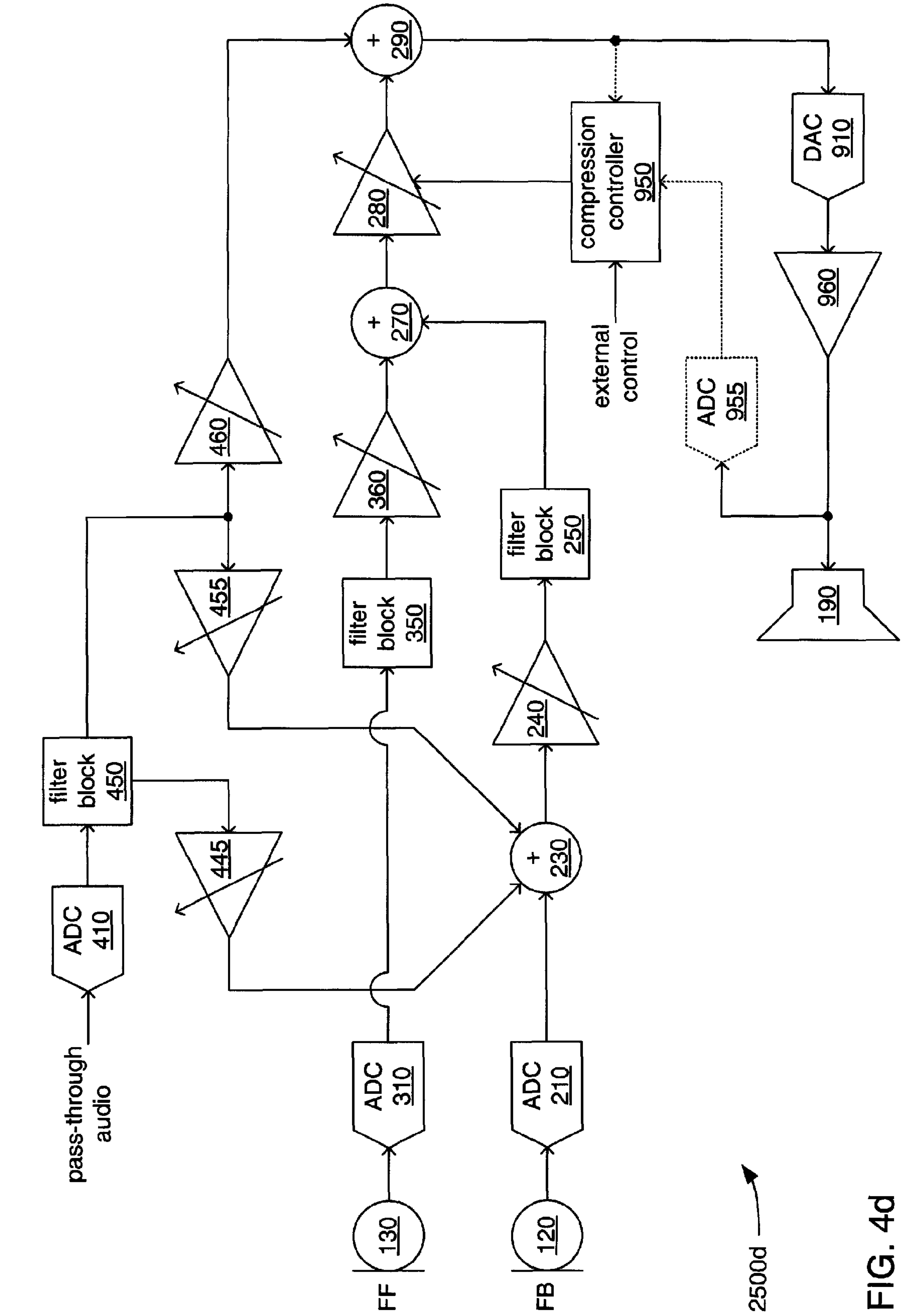

FIG. 4*d* depicts another possible signal processing topology 2500*d* for which the ANR circuit 2000 may be structured and/or programmed. Where the ANR circuit 2000 adopts the signal processing topology 2500*d*, the ANR circuit 2000 incorporates at least the DAC 910, the compression controller 950, the audio amplifier 960, the ADC 210, the summing nodes 230 and 290, the filter blocks 250 and 450, the VGA 280, and still other VGAs 445, 455 and 460. The ANR circuit 2000 may further incorporate one or more of the ADCs 310 and/or 410, the filter block 350, the summing node 270, the ADC 955, and still another VGA 360. The signal processing topologies 2500*c* and 2500*d* are similar in numerous ways. However, a substantial difference between the signal processing topologies 2500*c* and 2500*d* is the addition of the ability to direct the provision of the higher frequency sounds of the modified pass-through audio to be combined with other audio at either or both of two different locations within the signal processing topology 2500*d*.

One or more digital filters within the filter block 450 are employed to modify the digital data representing the pass-through audio to derive a modified variant of the pass-through audio data and to function as a crossover that divides the modified pass-through audio data into higher and lower frequency sounds. Data representing the lower frequency sounds are output to the summing node 230 through the VGA 445. Data representing the higher frequency sounds are output both to the summing node 230 through the VGA 455 and to the DAC 910 through the VGA 460. The VGAs 445, 455 and 460 are operable both to control the amplitudes of the lower frequency and higher frequency sounds represented by the data output by the filter block 450, and to selectively direct the flow of the data representing the higher frequency sounds. However, as has been previously discussed, the crossover functionality of the filter block 450 may be employed to selectively route the entirety of the modified pass-through audio to one or the other of the summing node 230 and the DAC 910.

Where the provision of feedforward-based ANR is also supported, the possible provision of higher frequency sounds (or perhaps the entirety of the modified pass-through audio) by the filter block 450 through the VGA 460 and to the DAC 910 may be through the summing node 290. The filter block 350 provides the feedforward anti-noise data to the summing node 270 through the VGA 360.

Figure 4E:
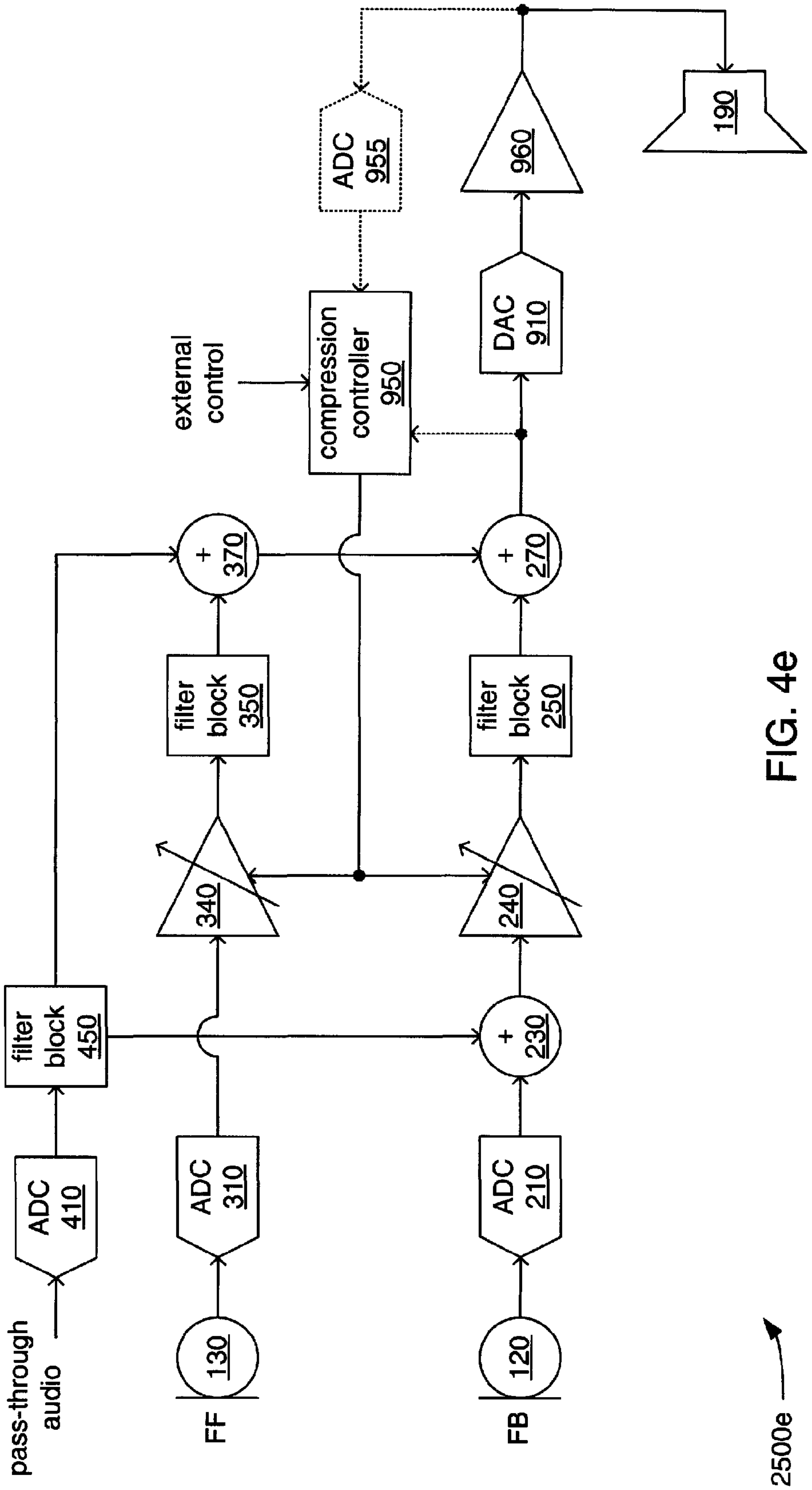
Figure 4F:
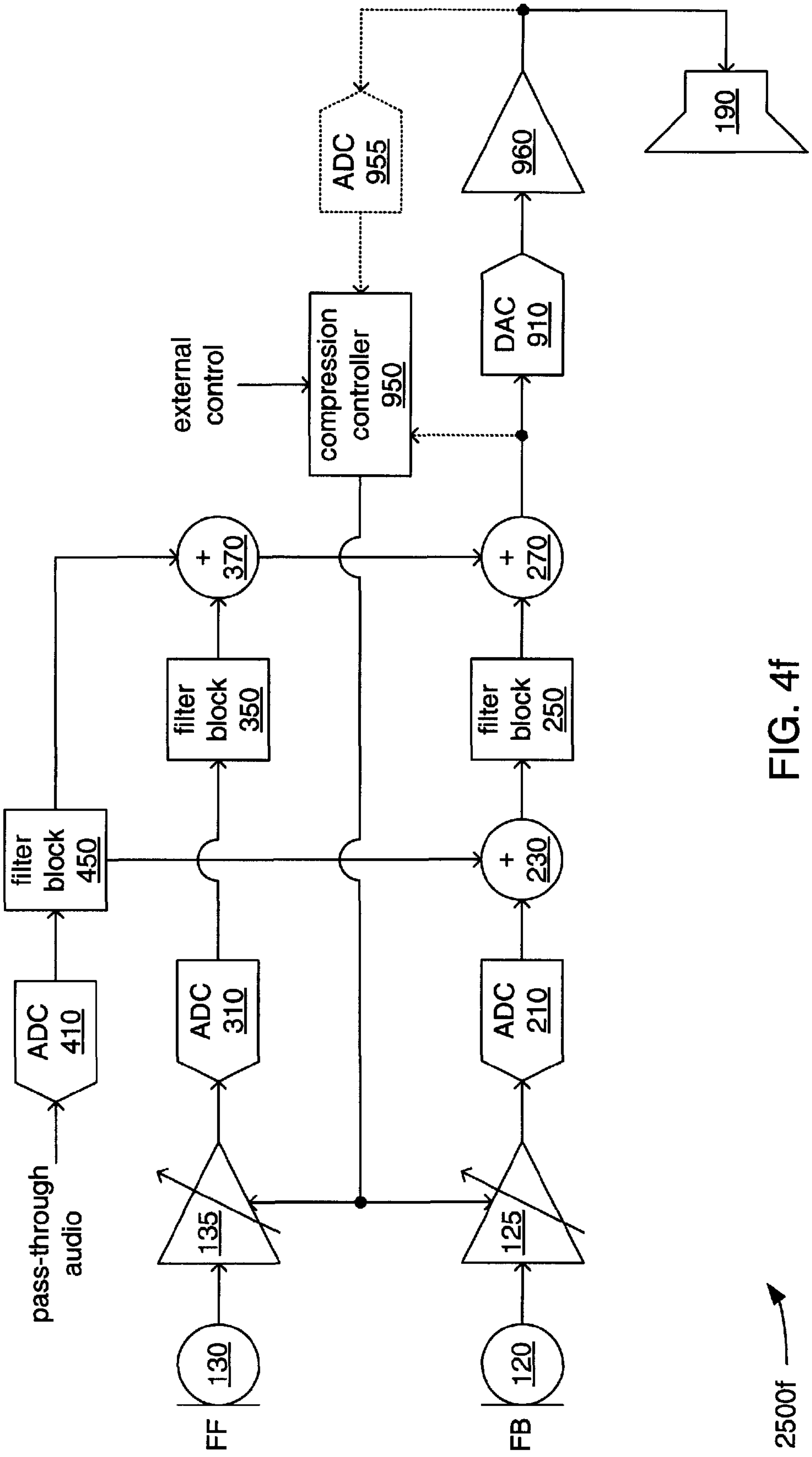
Figure 4G:
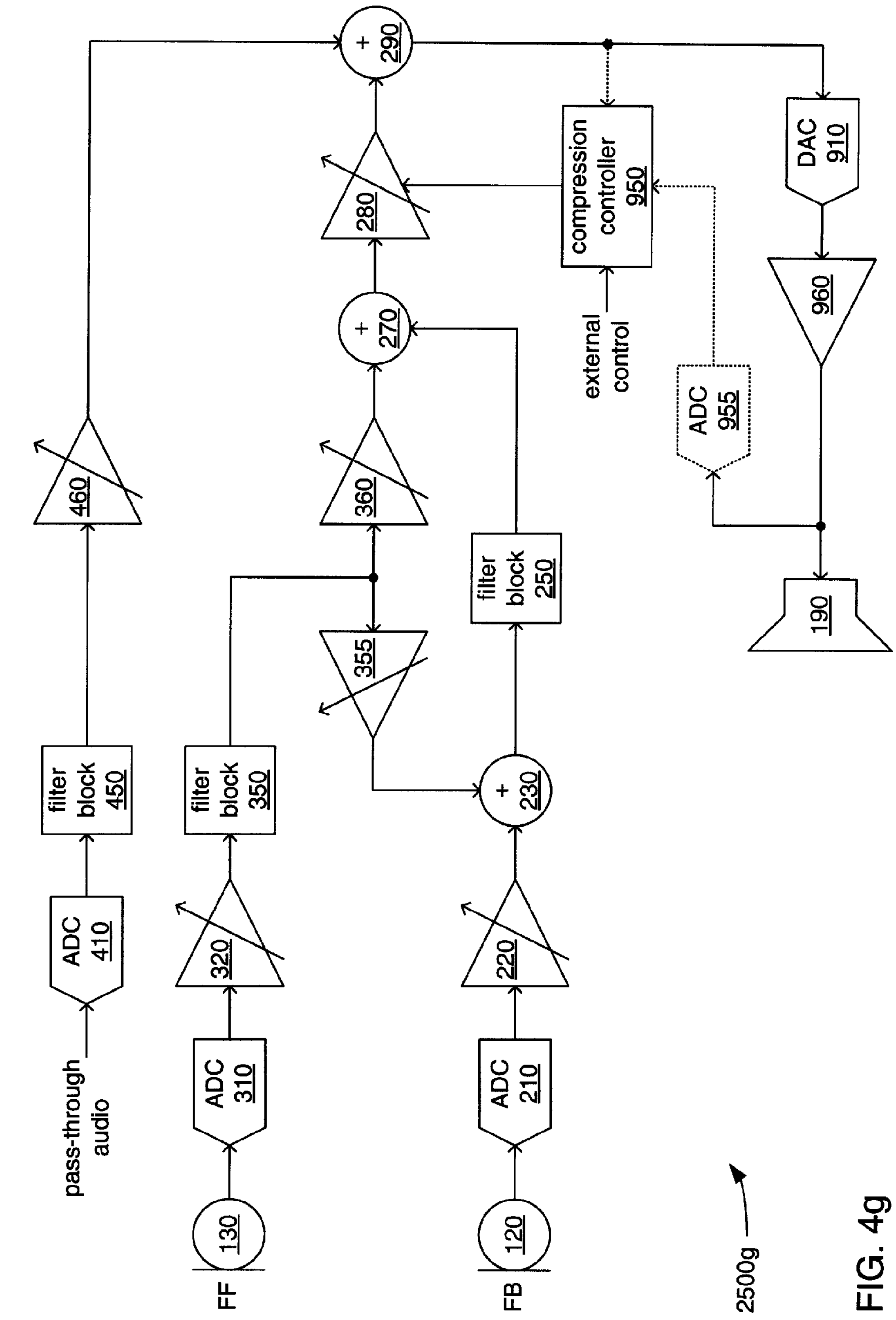

FIG. 4*e* depicts another possible signal processing topology 2500*e* for which the ANR circuit 2000 may be structured and/or programmed. Where the ANR circuit 2000 adopts the signal processing topology 2500*e*, the ANR circuit 2000 incorporates at least the DAC 910; the audio amplifier 960; the ADCs 210 and 310; the summing nodes 230, 270 and 370; the filter blocks 250, 350 and 450; the compressor 950; and a pair of VGAs 240 and 340. The ANR circuit 2000 may further incorporate one or both of the ADCs 410 and 955. The signal processing topologies 2500*b*, 2500*c* and 2500*e* are similar in numerous ways. The manner in which the data output by each of the filter blocks 250, 350 and 450 are combined in the signal processing topology 2500*e* is substantially similar to that of the signal processing topology 2500*b*. Also, like the signal processing topology 2500*c*, the signal processing topology 2500*e* incorporates the compression controller 950. However, a substantial difference between the signal processing topologies 2500*c* and 2500*e* is the replacement of the single VGA 280 in the signal processing topology 2500*c* for the separately controllable VGAs 240 and 340 in the signal processing topology 2500*e*.

The summing node 230 provides data representing feedback reference sounds possibly combined with data that may be output by the filter block 450 (perhaps the lower frequency sounds of the modified pass-through audio, or perhaps the entirety of the modified pass-through audio) to the filter block 250 through the VGA 240, and the ADC 310 provides data representing feedforward reference sounds to the filter block 350 through the VGA 340. The data output by the filter block 350 is combined with data that may be output by the filter block 450 (perhaps the higher frequency sounds of the modified pass-through audio, or perhaps the entirety of the modified pass-through audio) at the summing node 370. In turn, the summing node 370 provides its data to the summing node 270 to be combined with data output by the filter block 250. The summing node 270, in turn, provides its combined data to the DAC 910.

The compression controller 950 controls the gains of the VGAs 240 and 340, to enable the amplitude of the sounds represented by data output by the summing node 230 and the ADC 310, respectively, to be reduced in response to actual instances or indications of upcoming instances of clipping and/or other undesirable audio artifacts being detected by the compression controller 950. The gains of the VGAs 240 and 340 may be controlled in a coordinated manner, or may be controlled entirely independently of each other.

FIG. **4*f* depicts another possible signal processing topology 2500*f* for which the ANR circuit 2000 may be structured and/or programmed. Where the ANR circuit 2000 adopts the signal processing topology 2500*f*, the ANR circuit 2000 incorporates at least the DAC 910; the audio amplifier 960; the ADCs 210 and 310; the summing nodes 230, 270 and 370; the filter blocks 250, 350 and 450; the compressor 950; and the VGAs 125 and 135. The ANR circuit 2000 may further incorporate one or both of the ADCs 410 and 955. The signal processing topologies 2500*e* and 2500*f* are similar in numerous ways. However, a substantial difference between the signal processing topologies 2500*e* and 2500*f* is the replacement of the pair of VGAs 240 and 340 in the signal processing topology 2500*e* for the VGAs 125 and 135 in the signal processing topology 2500*f***.

The VGAs 125 and 135 positioned at the analog inputs to the ADCs 210 and 310, respectively, are analog VGAs, unlike the VGAs 240 and 340 of the signal processing topology **2500*e*. This enables the compression controller 950 to respond to actual occurrences and/or indications of soon-to-occur instances of clipping and/or other audio artifacts in driving the acoustic driver 190 by reducing the amplitude of one or both of the analog signals representing feedback and feedforward reference sounds. This may be deemed desirable where it is possible for the analog signals provided to the ADCs 210 and 310 to be at too great an amplitude such that clipping at the point of driving the acoustic driver 190 might be more readily caused to occur. The provision of the ability to reduce the amplitude of these analog signals (and perhaps also including the analog signal provided to the ADC 410 via the VGA 145 depicted elsewhere) may be deemed desirable to enable balancing of amplitudes between these analog signals, and/or to limit the numeric values of the digital data produced by one or more of the ADCs 210, 310 and 410** to lesser magnitudes to reduce storage and/or transmission bandwidth requirements.

FIG. **4*g* depicts another possible signal processing topology 2500*g* for which the ANR circuit 2000 may be programmed or otherwise structured. Where the ANR circuit 2000 adopts the signal processing topology 2500*g*, the ANR circuit 2000 incorporates at least the compression controller 950, the DAC 910, the audio amplifier 960, the ADCs 210 and 310, a pair of VGAs 220 and 320, the summing nodes 230 and 270, the filter blocks 250 and 350, another pair of VGAs 355 and 360, and the VGA 280. The ANR circuit 2000 may further incorporate one or more of the ADC 410, the filter block 450, still another VGA 460, the summing node 290, and the ADC 955**.

The ADC 210 receives an analog signal from the feedback microphone 120 and digitizes it, before providing corresponding feedback reference data to the VGA 220. The VGA 220 outputs the feedback reference data, possibly after modifying its amplitude, to the summing node 230. Similarly, the ADC 310 receives an analog signal from the feedforward microphone 130 and digitizes it, before providing corresponding feedforward reference data to the VGA 320. The VGA 320 outputs the feedforward reference data, possibly after modifying its amplitude, to the filter block 350. One or more digital filters within the filter block 350 are employed to modify the feedforward reference data to derive feedforward anti-noise data representing feedforward anti-noise sounds, and the filter block 350 provides the feedforward anti-noise data to both of the VGAs 355 and 360. In various implementations, the gains of the VGAs 355 and 360 are dynamically selectable and can be operated in a coordinated manner like a three-way switch to enable the feedforward anti-noise data to be selectively provided to either of the summing nodes 230 and 270. Thus, where the feedforward anti-noise data is combined with data related to feedback ANR within the signal processing topology **2500*g*** is made selectable.

Therefore, depending on the gains selected for the VGAs 355 and 360, the feedforward anti-noise data from the filter block 350 may be combined with the feedback reference data from the ADC 210 at the summing node 230, or may be combined with feedback anti-noise data derived by the filter block 250 from the feedback reference data at the summing node 270. If the feedforward anti-noise data is combined with the feedback reference data at the summing node 230, then the filter block 250 derives data representing a combination of feedback anti-noise sounds and further-modified feedforward anti-noise sounds, and this data is provided to the VGA 280 through the summing node 270 at which no combining of data occurs. Alternatively, if the feedforward anti-noise data is combined with the feedback anti-noise data at the summing node 270, then the feedback anti-noise data will have been derived by the filter block 250 from the feedback reference data received through the summing node 230 at which no combining of data occurs, and the data resulting from the combining at the summing node 270 is provided to the VGA 280. With or without an alteration in amplitude, the VGA 280 provides whichever form of combined data is received from the summing node 270 to the DAC 910 to create an analog signal. This provision of this combined data by the VGA 280 may be through the summing node 290 where the provision of pass-through audio is also supported.

Where the provision of pass-through audio is supported, the audio source 9400 may provide an analog signal representing pass-through audio to be acoustically output to a user, and the ADC 410 digitizes the analog signal and provides pass-through audio data corresponding to the analog signal to the filter block 450. Alternatively, where the audio source 9400 provides digital data representing pass-through audio, such digital data may be provided directly to the filter block 450. One or more digital filters within the filter block 450 may be employed to modify the digital data representing the pass-through audio to derive a modified variant of the pass-through audio data that may be re-equalized and/or enhanced in other ways. The filter block 450 provides the modified pass-through audio data to the VGA 460, and either with or without altering the amplitude of the pass-through audio sounds represented by the modified pass-through audio data, the VGA 460 provides the modified pass-through audio data to the DAC 910 through the summing node 290.

The compression controller 950 controls the gain of the VGA 280 to enable the amplitude of whatever combined form of feedback and feedforward anti-noise sounds are received by the VGA 280 to be reduced under the control of the compression controller 950 in response to actual occurrences and/or indications of impending instances of clipping and/or other audio artifacts.

FIGS. **5*a* through 5*e* depict some possible filter block topologies that may be employed in creating one or more blocks of filters (such as filter blocks 250, 350 and 450) within signal processing topologies adopted by the ANR circuit 2000 (such as the signal processing topologies 2500***a-g*). It should be noted that the designation of a multitude of digital filters as a "filter block" is an arbitrary construct meant to simplify the earlier presentation of signal processing topologies. In truth, the selection and positioning of one or more digital filters at any point along any of the pathways (such as the pathways 200, 300 and 400) of any signal processing topology may be accomplished in a manner identical to the selection and positioning of VGAs and summing nodes. Therefore, it is entirely possible for various digital filters to be positioned along a pathway for the movement of data in a manner in which those digital filters are interspersed among VGAs and/or summing nodes such that no distinguishable block of filters is created. Or, as will be illustrated, it is entirely possible for a filter block to incorporate a summing node or other component as part of the manner in which the filters of a filter block are coupled as part of the filter block topology of a filter block.

However, as previously discussed, multiple lower-order digital filters may be combined in various ways to perform the equivalent function of one or more higher-order digital filters. Thus, although the creation of distinct filter blocks is not necessary in defining a pathway having multiple digital filters, it can be desirable in numerous situations. Further, the creation of a block of filters at a single point along a pathway can more easily enable alterations in the characteristics of filtering performed in that pathway. By way of example, multiple lower-order digital filters connected with no other components interposed between them can be dynamically configured to cooperate to perform any of a variety of higher-order filter functions by simply changing their coefficients and/or changing the manner in which they are interconnected. Also, in some implementations, such close interconnection of digital filters may ease the task of dynamically configuring a pathway to add or remove digital filters with a minimum of changes to the interconnections that define that pathway.

It should be noted that the selections of types of filters, quantities of filters, interconnections of filters and filter block topologies depicted in each of FIGS. 5*a* through 5*e* are meant to serve as examples to facilitate understanding, and should not be taken as limiting the scope of what is described or the scope of what is claimed herein.

Figure 5A:
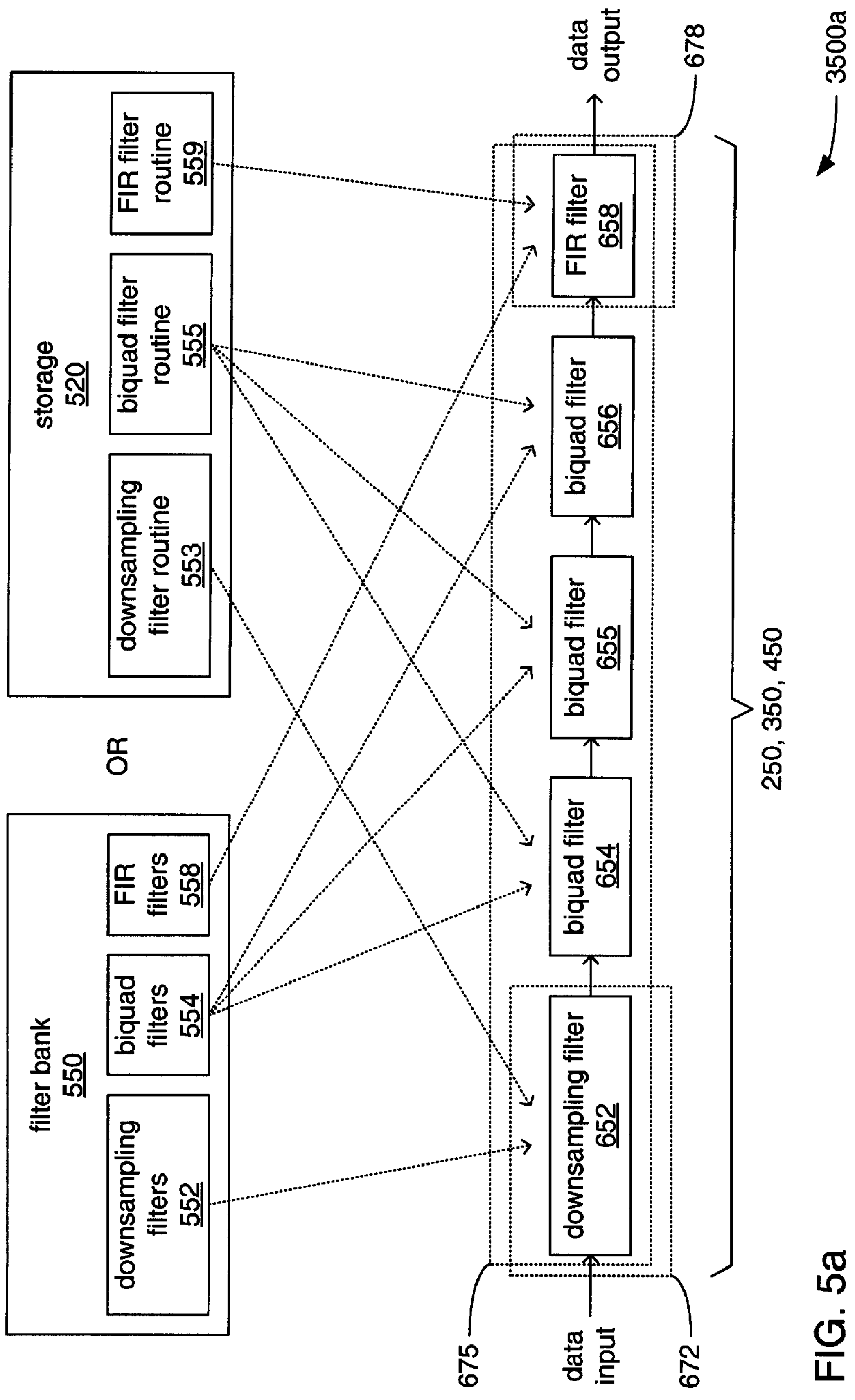
FIGS. 5*a* through 5*e* depict possible filter block topologies that may be adopted by the ANR circuit of the personal ANR device of FIG. 1.
Figure 6B:
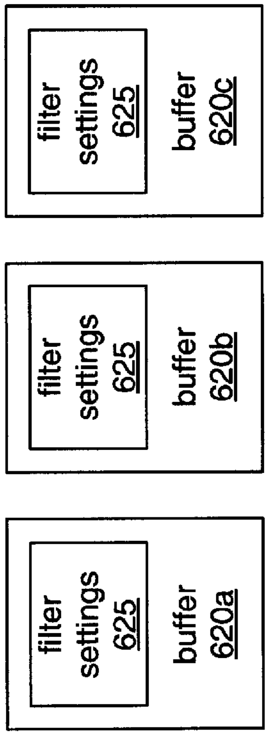
FIGS. 6*a* through 6*c* depict possible variants of triple-buffering that may be adopted by the ANR circuit of the personal ANR device of FIG. 1.
Figure 6A:
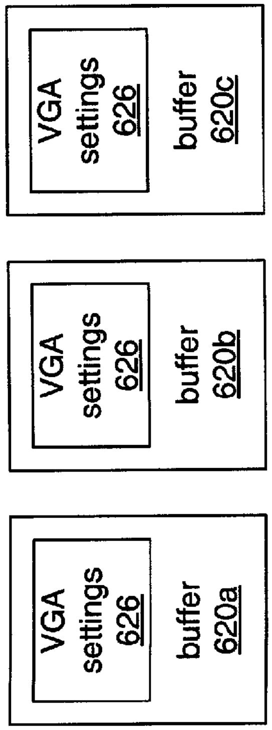
Figure 6C:
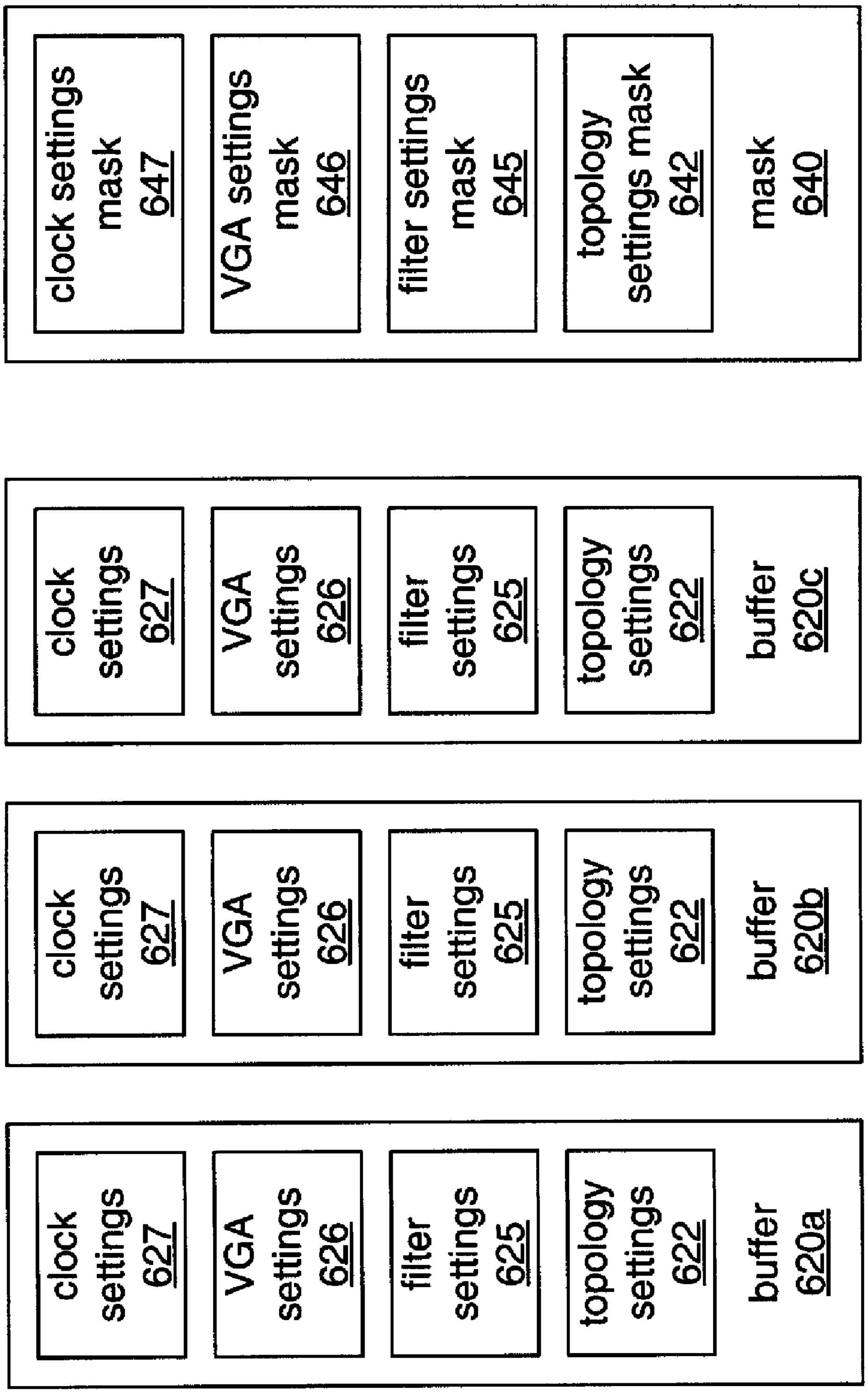

FIG. 5*a* depicts a possible filter block topology 3500*a* for which the ANR circuit 2000 may be structured and/or programmed to define a filter block, such as one of the filter blocks 250, 350 and 450. The filter block topology 3500*a* is made up of a serial chain of digital filters with a downsampling filter 652 at its input; biquad filters 654, 655 and 656; and a FIR filter 658 at its output.

As more explicitly depicted in FIG. 5*a*, in some implementations, the ANR circuit 2000 employs the internal architecture 2200*a* such that the ANR circuit 2000 incorporates the filter bank 550 incorporating multitudes of the downsampling filters 552, the biquad filters 554, and the FIR filters 558. One or more of each of the downsampling filters 552, biquad filters 554 and FIR filters 558 may be interconnected in any of a number of ways via the switch array 540, including in a way that defines the filter block topology 3500*a*. More specifically, the downsampling filter 652 is one of the downsampling filters 552; the biquad filters 654, 655 and 656 are each one of the biquad filters 554; and the FIR filter 658 is one of the FIR filters 558.

Alternatively, and as also more explicitly depicted in FIG. 5*a*, in other implementations, the ANR circuit 2000 employs the internal architecture 2200*b* such that the ANR circuit 2000 incorporates a storage 520 in which is stored the downsampling filter routine 553, the biquad filter routine 555 and the FIR filter routine 559. Varying quantities of downsampling, biquad and/or FIR filters may be instantiated within available storage locations of the storage 520 with any of a variety of interconnections defined between them, including quantities of filters and interconnections that define the filter block topology 3500*a*. More specifically, the downsampling filter 652 is an instance of the downsampling filter routine 553; the biquad filters 654, 655 and 656 are each instances of the biquad filter routine 555; and the FIR filter 658 is an instance of the FIR filter routine 559.

As previously discussed, power conservation and/or other benefits may be realized by employing different data transfer rates along different pathways of digital data representing sounds in a signal processing topology. In support of converting between different data transfer rates, including where one pathway operating at one data transfer rate is coupled to another pathway operating at another data transfer rate, different data transfer clocks may be provided to different ones of the digital filters within a filter block, and/or one or more digital filters within a filter block may be provided with multiple data transfer clocks.

By way of example, FIG. 5*a* depicts a possible combination of different data transfer rates that may be employed within the filter block topology 3500*a* to support digital data being received at one data transfer rate, digital data being transferred among these digital filters at another data transfer rate, and digital data being output at still another data transfer rate. More specifically, the downsampling filter 652 receives digital data representing a sound at a data transfer rate 672, and at least downsamples that digital data to a lower data transfer rate 675. The lower data transfer rate 675 is employed in transferring digital data among the downsampling filter 652, the biquad filters 654-656, and the FIR filter 658. The FIR filter 658 at least upsamples the digital data that it receives from the lower data transfer rate 675 to a higher data transfer rate 678 as that digital data is output by the filter block to which the digital filters in the filter block topology 3500*a* belong. Many other possible examples of the use of more than one data transfer rate within a filter block and the possible corresponding need to employ multiple data transfer clocks within a filter block will be clear to those skilled in the art.

Figure 5B:
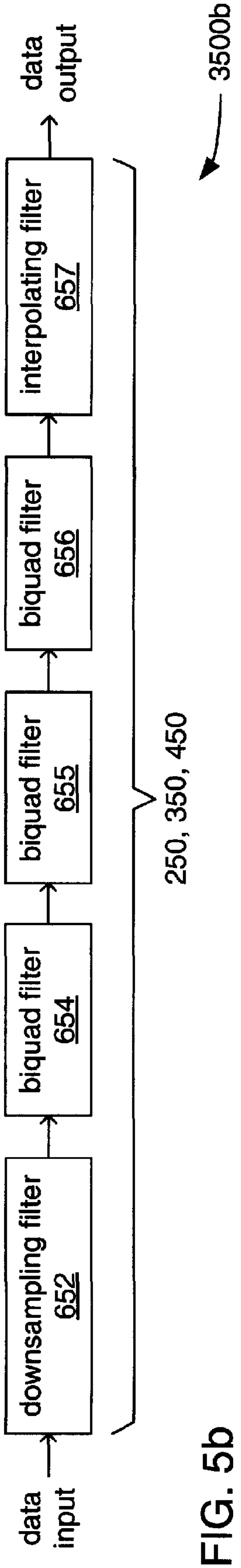

FIG. 5*b* depicts a possible filter block topology 3500*b* that is substantially similar to the filter block topology 3500*a*, but in which the FIR filter 658 of the filter block topology 3500*a* has been replaced with an interpolating filter 657. Where the internal architecture 2200*a* is employed, such a change from the filter block topology 3500*a* to the filter block topology 3500*b* entails at least altering the configuration of the switch array 540 to exchange one of the FIR filters 558 with one of the interpolating filters 556. Where the internal architecture 2200*b* is employed, such a change entails at least replacing the instantiation of the FIR filter routine 559 that provides the FIR filter 658 with an instantiation of the interpolating filter routine 557 to provide the interpolating filter 657

Figure 5C:
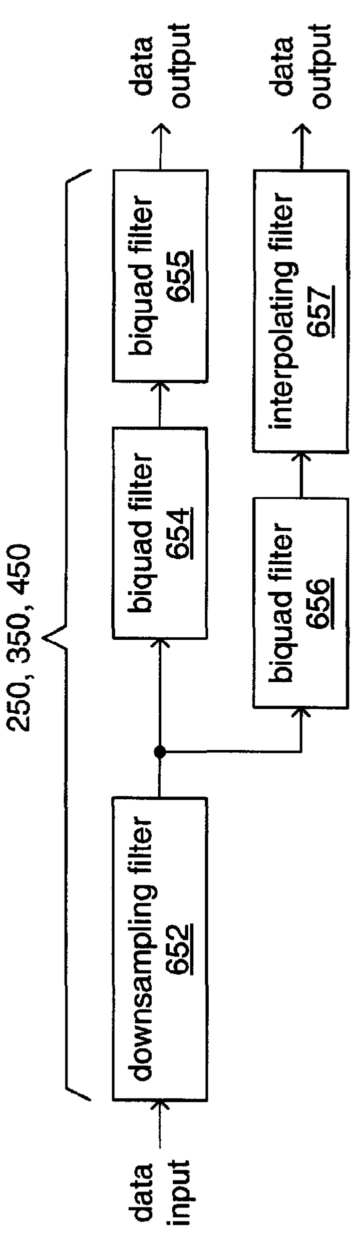

FIG. 5*c* depicts a possible filter block topology 3500*c* that is made up of the same digital filters as the filter block topology 3500*b*, but in which the interconnections between these digital filters have been reconfigured into a branching topology to provide two outputs, whereas the filter block topology 3500*b* had only one. Where the internal architecture 2200*a* is employed, such a change from the filter block topology 3500*b* to the filter block topology 3500*c* entails at least altering the configuration of the switch array 540 to disconnect the input to the biquad filter 656 from the output of the biquad filter 655, and to connect that input to the output of the downsampling filter 652, instead. Where the internal architecture 2200*b* is employed, such a change entails at least altering the instantiation of biquad filter routine 555 that provides the biquad filter 656 to receive its input from the instantiation of the downsampling filter routine 553 that provides the downsampling filter 652. The filter block topology 3500*c* may be employed where it is desired that a filter block be capable of providing two different outputs in which data representing audio provided at the input is altered in different ways to create two different modified versions of that data, such as in the case of the filter block 450 in each of the signal processing topologies 2500*b-f*.

Figure 5D:
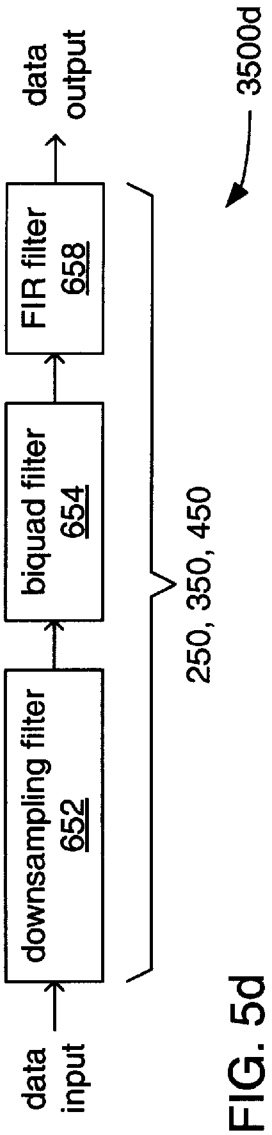

FIG. 5*d* depicts another possible filter block topology 3500*d* that is substantially similar to the filter block topology 3500*a*, but in which the biquad filters 655 and 656 have been removed to shorten the chain of digital filters from the quantity of five in the filter block topology 3500*a* to a quantity of three.

Figure 5E:
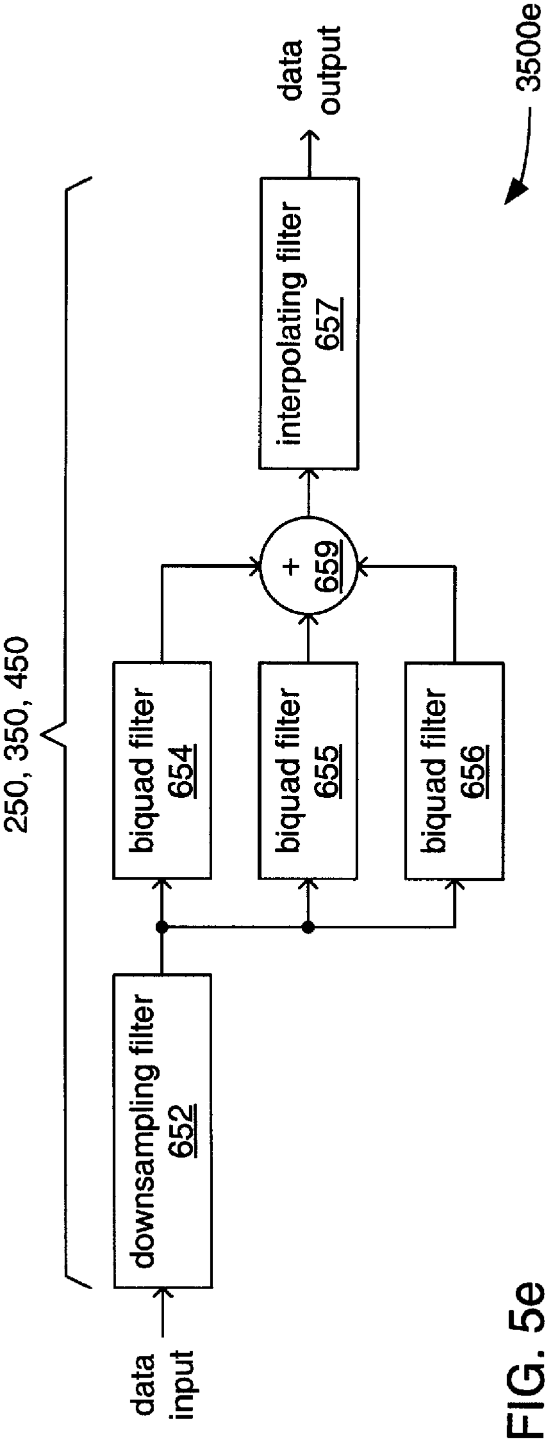

FIG. 5*e* depicts another possible filter block topology 3500*e* that is made up of the same digital filters as the filter block topology 3500*b*, but in which the interconnections between these digital filters have been reconfigured to put the biquad filters 654, 655 and 656 in a parallel configuration, whereas these same filters were in a serial chain configuration in the filter block topology 3500*b*. As depicted, the output of the downsampling filter 652 is coupled to the inputs of all three of the biquad filters 654, 655 and 656, and the outputs of all three of these biquad filters are coupled to the input of the interpolating filter 657 through an additionally incorporated summing node 659.

Taken together, the FIGS. 5*a* through 5*e* depict the manner in which a given filter block topology of a filter block is dynamically configurable to so as to allow the types of filters, quantities of filters and/or interconnections of digital filters to be altered during the operation of a filter block. However, as those skilled in the art will readily recognize, such changes in types, quantities and interconnections of digital filters are likely to require corresponding changes in filter coefficients and/or other settings to be made to achieve the higher-order filter function sought to be achieved with such changes. As will be discussed in greater detail, to avoid or at least mitigate the creation of audible distortions or other undesired audio artifacts arising from making such changes during the operation of the personal ANR device, such changes in interconnections, quantities of components (including digital filters), types of components, filter coefficients and/or VGA gain values are ideally buffered so as to enable their being made in a manner coordinated in time with one or more data transfer rates.

The dynamic configurability of both of the internal architectures 2200*a* and 2200*b*, as exemplified throughout the preceding discussion of dynamically configurable signal processing topologies and dynamically configurable filter block topologies, enables numerous approaches to conserving power and to reducing audible artifacts caused by the introduction of microphone self noise, quantization errors and other influences arising from components employed in the personal ANR device 1000. Indeed, there can be a synergy between achieving both goals, since at least some measures taken to reduce audible artifacts generated by the components of the personal ANR device 1000 can also result in reductions in power consumption. Reductions in power consumption can be of considerable importance given that the personal ANR device 1000 is preferably powered from a battery or other portable source of electric power that is likely to be somewhat limited in ability to provide electric power.

In either of the internal architectures 2200*a* and 2200*b*, the processing device 510 may be caused by execution of a sequence of instructions of the ANR routine 525 to monitor the availability of power from the power source 180. Alternatively and/or additionally, the processing device 510 may be caused to monitor characteristics of one or more sounds (e.g., feedback reference and/or anti-noise sounds, feedforward reference and/or anti-noise sounds, and/or pass-through audio sounds) and alter the degree of ANR provided in response to the characteristics observed. As those familiar with ANR will readily recognize, it is often the case that providing an increased degree of ANR often requires the implementation of a more complex transfer function, which often requires a greater number of filters and/or more complex types of filters to implement, and this in turn, often leads to greater power consumption. Analogously, a lesser degree of ANR often requires the implementation of a simpler transfer function, which often requires fewer and/or simpler filters, which in turn, often leads to less power consumption.

Further, there can arise situations, such as an environment with relatively low environmental noise levels or with environmental noise sounds occurring within a relatively narrow range of frequencies, where the provision of a greater degree of ANR can actually result in the components used in providing the ANR generating noise sounds greater than the attenuated environmental noise sounds. Still further, and as will be familiar to those skilled in the art of feedback-based ANR, under some circumstances, providing a considerable degree of feedback-based ANR can lead to instability as undesirable audible feedback noises are produced.

In response to either an indication of diminishing availability of electric power or an indication that a lesser degree of ANR is needed (or is possibly more desirable), the processing device 510 may disable one or more functions (including one or both of feedback-based and feedforward-based ANR), lower data transfer rates of one or more pathways, disable branches within pathways, lower data transfer rates between digital filters within a filter block, replace digital filters that consume more power with digital filters that consume less power, reduce the complexity of a transfer function employed in providing ANR, reduce the overall quantity of digital filters within a filter block, and/or reduce the gain to which one or more sounds are subjected by reducing VGA gain settings and/or altering filter coefficients. However, in taking one or more of these or other similar actions, the processing device 510 may be further caused by the ANR routine 525 to estimate a degree of reduction in the provision of ANR that balances one or both of the goals of reducing power consumption and avoiding the provision of too great a degree of ANR with one or both of the goals of maintaining a predetermined desired degree of quality of sound and quality of ANR provided to a user of the personal ANR device 1000. A minimum data transfer rate, a maximum signal-to-noise ratio or other measure may be used as the predetermined degree of quality or ANR and/or sound.

As an example, and referring back to the signal processing topology 2500*a* of FIG. 4*a* in which the pathways 200, 300 and 400 are explicitly depicted, a reduction in the degree of ANR provided and/or in the consumption of power may be realized through turning off one or more of the feedback-based ANR, feedforward-based ANR and pass-through audio functions. This would result in at least some of the components along one or more of the pathways 200, 300 and 400 either being operated to enter a low power state in which operations involving digital data would cease within those components, or being substantially disconnected from the power source 180. A reduction in power consumption and/or degree of ANR provided may also be realized through lowering the data transfer rate(s) of at least portions of one or more of the pathways 200, 300 and 400, as previously discussed in relation to FIG. 4*a*.

As another example, and referring back to the signal processing topology 2500*b* of FIG. 4*b* in which the pathways 200, 300 and 400 are also explicitly depicted, a reduction in power consumption and/or in the complexity of transfer functions employed may be realized through turning off the flow of data through one of the branches of the split in the pathway 400. More specifically, and as previously discussed in relation to FIG. 4*b*, the crossover frequency employed by the digital filters within the filter block 450 to separate the modified pass-through audio into higher frequency and lower frequency sounds may be selected to cause the entirety of the modified pass-through audio to be directed towards only one of the branches of the pathway 400. This would result in discontinuing of the transfer of modified pass-through audio data through one or the other of the summing nodes 230 and 370, thereby enabling a reduction in power consumption and/or in the introduction of noise sounds from components by allowing the combining function of one or the other of these summing nodes to be disabled or at least to not be utilized. Similarly, and referring back to the signal processing topology 2500*d* of FIG. 4*d* (despite the lack of explicit marking of its pathways), either the crossover frequency employed by the filter block 450 or the gain settings of the VGAs 445, 455 and 460 may be selected to direct the entirety of the modified pass-through audio data down a single one of the three possible pathway branches into which each of these VGAs lead. Thus, a reduction in power consumption and/or in the introduction of noise sounds would be enabled by allowing the combining function of one or the other of the summing nodes 230 and 290 to be disabled or at least not be utilized. Still further, one or more of the VGAs 445, 455 and 460 through which modified pass-through audio data is not being transferred may be disabled.

As still another example, and referring back to the filter block topology 3500*a* of FIG. 5*a* in which the allocation of three data transfer rates 672, 675 and 678 are explicitly depicted, a reduction in the degree of ANR provided and/or in power consumption may be realized through lowering one or more of these data transfer rates. More specifically, within a filter block adopting the filter block topology 3500*a*, the data transfer rate 675 at which digital data is transferred among the digital filters 652, 654-656 and 658 may be reduced. Such a change in a data transfer rate may also be accompanied by exchanging one or more of the digital filters for variations of the same type of digital filter that are better optimized for lower bandwidth calculations. As will be familiar to those skilled in the art of digital signal processing, the level of calculation precision required to maintain a desired predetermined degree of quality of sound and/or quality of ANR in digital processing changes as sampling rate changes. Therefore, as the data transfer rate 675 is reduced, one or more of the biquad filters 654-656 which may have been optimized to maintain a desired degree of quality of sound and/or desired degree of quality of ANR at the original data transfer rate may be replaced with other variants of biquad filter that are optimized to maintain substantially the same quality of sound and/or ANR at the new lower data transfer rate with a reduced level of calculation precision that also reduces power consumption. This may entail the provision of different variants of one or more of the different types of digital filter that employ coefficient values of differing bit widths and/or incorporate differing quantities of taps.

As still other examples, and referring back to the filter block topologies 3500*c* and 3500*d* of FIGS. 5*c* and 5*d*, respectively, as well as to the filter block topology 3500*a*, a reduction in the degree of ANR provided and/or in power consumption may be realized through reducing the overall quantity of digital filters employed in a filter block. More specifically, the overall quantity of five digital filters in the serial chain of the filter block topology 3500*a* may be reduced to the overall quantity of three digital filters in the shorter serial chain of the filter block topology 3500*d*. As those skilled in the art would readily recognize, such a change in the overall quantity of digital filters would likely need to be accompanied by a change in the coefficients provided to the one or more of the digital filters that remain, since it is likely that the transfer function(s) performed by the original five digital filters would have to be altered or replaced by transfer function(s) that are able to be performed with the three digital filters that remain. Also more specifically, the overall quantity of five digital filters in the branching topology of the filter block topology 3500*c* may be reduced to an overall quantity of three digital filters by removing or otherwise deactivating the filters of one of the branches (e.g., the biquad filter 656 and the interpolating filter 657 of one branch that provides one of the two outputs). This may be done in concert with selecting a crossover frequency for a filter block providing a crossover function to effectively direct all frequencies of a sound represented by digital data to only one of the two outputs, and/or in concert with operating one or more VGAs external to a filter block to remove or otherwise cease the transfer of digital data through a branch of a signal processing topology.

Reductions in data transfer rates may be carried out in various ways in either of the internal architectures 2200*a* and 2200*b*. By way of example in the internal architecture 2200*a*, various ones of the data transfer clocks provided by the clock bank 570 may be directed through the switch array 540 to differing ones of the digital filters, VGAs and summing nodes of a signal processing topology and/or filter block topology to enable the use of multiple data transfer rates and/or conversions between different data transfer rates by one or more of those components. By way of example in the internal architecture 2200*b*, the processing device 510 may be caused to execute the sequences of instructions of the various instantiations of digital filters, VGAs and summing nodes of a signal processing topology and/or filter block topology at intervals of differing lengths of time. Thus, the sequences of instructions for one instantiation of a given component are executed at more frequent intervals to support a higher data transfer rate than the sequences of instructions for another instantiation of the same component where a lower data transfer rate is supported.

As yet another example, and referring back to any of the earlier-depicted signal processing topologies and/or filter block topologies, a reduction in the degree of ANR provided and/or in power consumption may be realized through the reduction of the gain to which one or more sounds associated with the provision of ANR (e.g., feedback reference and/or anti-noise sounds, or feedforward reference and/or anti-noise sounds). Where a VGA is incorporated into at least one of a feedback-based ANR pathway and a feedforward-based ANR pathway, the gain setting of that VGA may be reduced. Alternatively and/or additionally, and depending on the transfer function implemented by a given digital filter, one or more coefficients of that digital filter may be altered to reduce the gain imparted to whatever sounds are represented by the digital data output by that digital filter. As will be familiar to those skilled in the art, reducing a gain in a pathway can reduce the perceptibility of noise sounds generated by components. In a situation where there is relatively little in the way of environmental noise sounds, noise sounds generated by components can become more prevalent, and thus, reducing the noise sounds generated by the components can become more important than generating anti-noise sounds to attenuate what little in the way of environmental noise sounds may be present. In some implementations, such reduction(s) in gain in response to relatively low environmental noise sound levels may enable the use of lower cost microphones.

In some implementations, performing such a reduction in gain at some point along a feedback-based ANR pathway may prove more useful than along a feedforward-based ANR pathway, since environmental noise sounds tend to be more attenuated by the PNR provided by the personal ANR device before ever reaching the feedback microphone 120. As a result of the feedback microphone 120 tending to be provided with weaker variants of environmental noise sounds than the feedforward microphone 130, the feedback-based ANR function may be more easily susceptible to a situation in which noise sounds introduced by components become more prevalent than environmental noise sounds at times when there is relatively little in the way of environmental noise sounds. A VGA may be incorporated into a feedback-based ANR pathway to perform this function by normally employing a gain value of 1 which would then be reduced to ½ or to some other preselected lower value in response to the processing device 510 and/or another processing device external to the ANR circuit 2000 and to which the ANR circuit 2000 is coupled determining that environmental noise levels are low enough that noise sounds generated by components in the feedback-based ANR pathway are likely to be significant enough that such a gain reduction is more advantageous than the production of feedback anti-noise sounds.

The monitoring of characteristics of environmental noise sounds as part of determining whether or not changes in ANR settings are to be made may entail any of a number of approaches to measuring the strength, frequencies and/or other characteristics of the environmental noise sounds. In some implementations, a simple sound pressure level (SPL) or other signal energy measurement without weighting may be taken of environmental noise sounds as detected by the feedback microphone 120 and/or the feedforward microphone 130 within a preselected range of frequencies. Alternatively, the frequencies within the preselected range of frequencies of a SPL or other signal energy measurement may subjected to the widely known and used "A-weighted" frequency weighting curve developed to reflect the relative sensitivities of the average human ear to different audible frequencies.

FIGS. 6*a* through 6*c* depict aspects and possible implementations of triple-buffering both to enable synchronized ANR setting changes and to enable a failsafe response to an occurrence and/or to indications of a likely upcoming occurrence of an out-of-bound condition, including and not limited to, clipping and/or excessive amplitude of acoustically output sounds, production of a sound within a specific range of frequencies that is associated with a malfunction, instability of at least feedback-based ANR, or other condition that may generate undesired or uncomfortable acoustic output. Each of these variations of triple-buffering incorporate at least a trio of buffers 620*a*, 620*b* and 620*c*. In each depicted variation of triple-buffering, two of the buffers 620*a* and 620*b* are alternately employed during normal operation of the ANR circuit 2000 to synchronously update desired ANR settings "on the fly," including and not limited to, topology interconnections, data clock settings, data width settings, VGA gain settings, and filter coefficient settings. Also, in each depicted variation of triple-buffering, the third buffer 620*c* maintains a set of ANR settings deemed to be "conservative" or "failsafe" settings that may be resorted to bring the ANR circuit 2000 back into stable operation and/or back to safe acoustic output levels in response to an out-of-bound condition being detected.

As will be familiar to those skilled in the art of controlling digital signal processing for audio signals, it is often necessary to coordinate the updating of various audio processing settings to occur during intervals between the processing of pieces of audio data, and it is often necessary to cause the updating of at least some of those settings to be made during the same interval. Failing to do so can result in the incomplete programming of filter coefficients, an incomplete or malformed definition of a transfer function, or other mismatched configuration issue that can result in undesirable sounds being created and ultimately acoustically output, including and not limited to, sudden popping or booming noises that can surprise or frighten a listener, sudden increases in volume that are unpleasant and can be harmful to a listener, or howling feedback sounds in the case of updating feedback-based ANR settings that can also be harmful.

In some implementations, the buffers 620*a-c* of any of FIGS. 6*a-c* are dedicated hardware-implemented registers, the contents of which are able to be clocked into registers within the VGAs, the digital filters, the summing nodes, the clocks of the clock bank 570 (if present), switch array 540 (if present), the DMA device 541 (if present) and/or other components. In other implementations, the buffers 620*a-c* of FIGS. 6*a-c* are assigned locations within the storage 520, the contents of which are able to be retrieved by the processing device 510 and written by the processing device 510 into other locations within the storage 520 associated with instantiations of the VGAs, digital filters, and summing nodes, and/or written by the processing device 510 into registers within the clocks of the clock bank 570 (if present), the switch array 540 (if present), the DMA device 541 (if present) and/or other components.

FIG. 6*a* depicts the triple-buffering of VGA settings, including gain values, employing variants of the buffers 620*a-c* that each store differing ones of VGA settings 626. An example of a use of such triple-buffering of VGA gain values may be the compression controller 950 operating one or more VGAs to reduce the amplitude of sounds represented by digital data in response to detecting occurrences and/or indications of impending occurrences of clipping and/or other audible artifacts in the acoustic output of the acoustic driver 190. In some implementations, the compression controller 950 stores new VGA settings into a selected one of the buffers 620*a* and 620*b*. At a subsequent time that is synchronized to the flow of pieces of digital data through one or more of the VGAs, the settings stored in the selected one of the buffers 620*a* and 620*b* are provided to those VGAs, thereby avoiding the generation of audible artifacts. As those skilled in the art will readily recognize, the compression controller 950 may repeatedly update the gain settings of VGAs over a period of time to "ramp down" the amplitude of one or more sounds to a desired level of amplitude, rather than to immediately reduce the amplitude to that desired level. In such a situation, the compression controller 950 would alternate between storing updated gain settings to the buffer 620*a* and storing updated gain settings to the buffer 620*b*, thereby enabling the decoupling of the times at which each of the buffers 620*a* and 620*b* are each written to by the compression controller 950 and the times at which each of the buffers provide their stored VGA settings to the VGAs. However, a set of more conservatively selected VGA settings is stored in the buffer 620*c*, and these failsafe settings may be provided to the VGAs in response to an out-of-bound condition being detected. Such provision of the VGA settings stored in the buffer 620*c* overrides the provision of any VGA settings stored in either of the buffers 620*a* and 620*b*.

FIG. 6*b* depicts the triple-buffering of filter settings, including filter coefficients, employing variants of the buffers 620*a-c* that each store differing ones of filter settings 625. An example of a use of such triple-buffering of filter coefficients may be adjusting the range of frequencies and/or the degree of attenuation of noise sounds that are reduced in the feedback-based ANR provided by the personal ANR device 1000. In some implementations, processing device 510 is caused by the ANR routine 525 to store new filter coefficients into a selected one of the buffers 620*a* and 620*b*. At a subsequent time that is synchronized to the flow of pieces of digital data through one or more of the digital filters, the settings stored in the selected one of the buffers 620*a* and 620*b* are provided to those digital filters, thereby avoiding the generation of audible artifacts. Another example of a use of such triple-buffering of filter coefficients may be adjusting the crossover frequency employed by the digital filters within the filter block 450 in some of the above signal processing topologies to divide the sounds of the modified pass-through audio into lower and higher frequency sounds. At a time synchronized to at least the flow of pieces of digital data associated with pass-through audio through the digital filters of the filter block 450, filter settings stored in one or the other of the buffers 620*a* and 620*b* are provided to at least some of the digital filters.

FIG. 6*c* depicts the triple-buffering of either all or a selectable subset of clock, VGA, filter and topology settings, employing variants of the buffers 620*a-c* that each store differing ones of topology settings 622, filter settings 625, VGA settings 626 and clock settings 627. An example of a use of triple-buffering of all of these settings may be changing from one signal processing topology to another in response to a user of the personal ANR device 1000 operating a control to activate a "talk-through" feature in which the ANR provided by the personal ANR device 1000 is altered to enable the user to more easily hear the voice of another person without having to remove the personal ANR device 1000 or completely turn off the ANR function. The processing device 510 may be caused to store the settings required to specify a new signal processing topology in which voice sounds are more readily able to pass to the acoustic driver 190 from the feedforward microphone 130, and the various settings of the VGAs, digital filters, data clocks and/or other components of the new signal processing topology within one or the other of the buffers 620*a* and 620*b*. Then, at a time synchronized to the flow of at least some pieces of digital data representing sounds through at least one component (e.g., an ADC, a VGA, a digital filter, a summing node, or a DAC), the settings are used to create the interconnections for the new signal processing topology (by being provided to the switch array 540, if present) and are provided to the components that are to be used in the new signal processing topology.

However, some variants of the triple-buffering depicted in FIG. 6*c* may further incorporate a mask 640 providing the ability to determine which settings are actually updated as either of the buffers 620*a* and 620*b* provide their stored contents to one or more components. In some embodiments, bit locations within the mask are selectively set to either 1 or 0 to selectively enable the contents of different ones of the settings corresponding to each of the bit locations to be provided to one or more components when the contents of one or the other of the buffers 620*a* and 620*b* are to provide updated settings to the components. The granularity of the mask 640 may be such that each individual setting may be selectively enabled for updating, or may be such that the entirety of each of the topology settings 622, the filter settings 625, the VGA setting 626 and the clock setting 627 are able to be selected for updating through the topology settings mask 642, the filter settings mask 645, the VGA settings mask 646 and the clock settings mask 647, respectively.

Other implementations are within the scope of the following claims and other claims to which the applicant may be entitled.

The invention claimed is:

1. A personal ANR device comprising:

a first earpiece;

a first feedback microphone disposed within the first earpiece;

a first feedforward microphone disposed on an external portion of the personal ANR device;

a first acoustic driver disposed within the first earpiece; and a first ANR circuit structured to:

receive a first feedback reference signal representing feedback reference sounds from the first feedback microphone;

generate first feedback anti-noise sounds from digital data representing at least the first feedback reference signal;

receive a first feedforward reference signal from the first feedforward microphone;

generate first feedforward anti-noise sounds from digital data representing at least the first feedforward reference signal;

receive a pass-through audio signal from an audio source;

generate first modified pass-through audio sounds from digital data representing at least the pass-through audio signal;

split the first modified pass-through audio sounds into lower frequency sounds and higher frequency sounds at a crossover frequency;

combine the lower frequency sounds with one of the feedback reference sounds and the feedback anti-noise sounds, and combine the higher frequency sounds with the other one of the feedback reference sounds and the feedback anti-noise sounds, wherein the selectable crossover frequency may be selected to route the entirety of the modified pass-through audio sounds to be combined with one of the feedback reference sounds and the feedback anti-noise sounds; and output a first output signal conveying the first feedback anti-noise sounds, the first feedforward anti-noise sounds and the first modified pass-through audio sounds to be acoustically output by the first acoustic driver.

2. The personal ANR device of claim 1, further comprising the audio source, wherein the audio source is an audio playback device disposed within the personal ANR device.

3. A personal ANR device comprising:

a first earpiece;

a first feedback microphone disposed within the first earpiece;

a first feedforward microphone disposed on an external portion of the personal ANR device;

a first acoustic driver disposed within the first earpiece;

a first ANR circuit structured to:

receive a first feedback reference signal from the first feedback microphone;

generate first feedback anti-noise sounds from digital data representing at least the first feedback reference signal;

receive a first feedforward reference signal from the first feedforward microphone;

generate first feedforward anti-noise sounds from digital data representing at least the first feedforward reference signal;

receive a pass-through audio signal from an audio source;

generate first modified pass-through audio sounds from digital data representing at least the pass-through audio signal; and output a first output signal conveying the first feedback anti-noise sounds, the first feedforward anti-noise sounds and the first modified pass-through audio sounds to be acoustically output by the first acoustic driver; and wherein the audio source is a communications microphone disposed on a portion of the personal ANR device in the vicinity of a mouth of a user of the personal ANR device to detect speech sounds emanating from the user.

4. The personal ANR device of claim 3, further comprising:

a second earpiece;

a second feedback microphone disposed within the second earpiece; and a second acoustic driver disposed within the second earpiece.

5. The personal ANR device of claim 4, wherein the first ANR circuit is further structured to:

receive a second feedback reference signal from the second feedback microphone;

generate second feedback anti-noise sounds from digital data representing at least the second feedback reference signal;

generate second feedforward anti-noise sounds from digital data representing at least the first feedforward reference signal;

generate second modified pass-through audio sounds from digital data representing at least the pass-through audio signal; and output a second output signal conveying the second feedback anti-noise sounds, the second feedforward anti-noise sounds and the second modified pass-through audio sounds to be acoustically output by the second acoustic driver.

6. The personal ANR device of claim 4, further comprising a second feedforward microphone disposed on an external portion of the personal ANR device, and wherein the first ANR circuit is further structured to:

receive a second feedback reference signal from the second feedback microphone;

generate second feedback anti-noise sounds from digital data representing at least the second feedback reference signal;

receive a second feedforward reference signal from the second feedforward microphone;

generate second feedforward anti-noise sounds from digital data representing at least the second feedforward reference signal;

generate second modified pass-through audio sounds from digital data representing at least the pass-through audio signal; and output a second output signal conveying the second feedback anti-noise sounds, the second feedforward anti-noise sounds and the second modified pass-through audio sounds to be acoustically output by the second acoustic driver.

7. The personal ANR device of claim 4, further comprising:

a second feedforward microphone disposed on an external portion of the personal ANR device; and a second ANR circuit structured to:

receive a second feedback reference signal from the second feedback microphone;

generate second feedback anti-noise sounds from digital data representing at least the second feedback reference signal;

receive a second feedforward reference signal from the second feedforward microphone;

generate second feedforward anti-noise sounds from digital data representing at least the second feedforward reference signal;

receive the pass-through audio signal from the audio source;

generate second modified pass-through audio sounds from digital data representing at least the pass-through audio signal; and output a second signal conveying the second feedback anti-noise sounds, the second feedforward anti-noise sounds and the second modified pass-through audio sounds to be acoustically output by the second acoustic driver.

8. An ANR circuit comprising a signal processing topology having a feedback ANR pathway, a feedforward ANR pathway, and a pass-through audio pathway, wherein the ANR circuit is structured to:

receive a feedback reference signal representing feedback reference sounds from a feedback microphone;

generate feedback anti-noise sounds in the feedback ANR pathway from digital data representing at least the feedback reference signal;

receive a feedforward reference signal from a feedforward microphone;

generate feedforward anti-noise sounds in the feedforward ANR pathway from digital data representing at least the feedforward reference signal;

receive a pass-through audio signal from an audio source;

generate modified pass-through audio sounds in the pass-through audio pathway from digital data representing the pass-through audio signal;

split the first modified pass-through audio sounds into lower frequency sounds and higher frequency sounds at a crossover frequency;

combine the lower frequency sounds with one of the feedback reference sounds at a first location along the feedback ANR pathway and the feedback anti-noise sounds at a second location along the feedback ANR pathway, and combine the higher frequency sounds with the other one of the feedback reference sounds at the first location and the feedback anti-noise sounds at the second location, wherein the selectable crossover frequency may be selected to route the entirety of the modified pass-through audio sounds to be combined with one of the feedback reference sounds at the first location and the feedback anti-noise sounds at the second location; and combine the feedback anti-noise sounds from the feedback ANR pathway and the feedforward anti-noise sounds from the feedforward ANR pathway; and output an output signal conveying a combination of the feedback anti-noise sounds, the feedforward anti-noise sounds and the modified pass-through audio sounds to be acoustically output by an acoustic driver.

9. An ANR circuit comprising a signal processing topology having a feedback ANR pathway, a feedforward ANR pathway, and a pass-through audio pathway, wherein the ANR circuit is structured to:

receive a feedback reference signal from a feedback microphone;

generate feedback anti-noise sounds in the feedback ANR pathway from digital data representing at least the feedback reference signal;

receive a feedforward reference signal from a feedforward microphone;

generate feedforward anti-noise sounds in the feedforward ANR pathway from digital data representing at least the feedforward reference signal;

receive a pass-through audio signal from an audio source;

generate modified pass-through audio sounds in the pass-through audio pathway from digital data representing the pass-through audio signal;

combine the feedback anti-noise sounds from the feedback ANR pathway, the feedforward anti-noise sounds from the feedforward ANR pathway, and the modified pass-through audio sounds from the pass-through audio pathway;

output an output signal conveying a combination of the feedback anti-noise sounds, the feedforward anti-noise sounds and the modified pass-through audio sounds to be acoustically output by an acoustic driver; and enable a point at which the feedforward anti-noise sounds are combined with the feedback anti-noise sounds to be selectable between at least a first location along the feedback ANR pathway where the feedback ANR and feedforward ANR pathways are able to be combined and a second location along the feedback ANR pathway where the feedback ANR and feedforward ANR pathways are able to be combined.

10. An ANR circuit comprising a signal processing topology having a feedback ANR pathway, a feedforward ANR pathway, and a pass-through audio pathway, wherein the ANR circuit is structured to:

receive a feedback reference signal from a feedback microphone;

generate feedback anti-noise sounds in the feedback ANR pathway from digital data representing at least the feedback reference signal;

receive a feedforward reference signal from a feedforward microphone;

generate feedforward anti-noise sounds in the feedforward ANR pathway from digital data representing at least the feedforward reference signal;

receive a pass-through audio signal from an audio source;

generate modified pass-through audio sounds in the pass-through audio pathway from digital data representing the pass-through audio signal;

combine the feedback anti-noise sounds from the feedback ANR pathway, the feedforward anti-noise sounds from the feedforward ANR pathway, and the modified pass-through audio sounds from the pass-through audio pathway;

output an output signal conveying a combination of the feedback anti-noise sounds, the feedforward anti-noise sounds and the modified pass-through audio sounds to be acoustically output by an acoustic driver; and enable a point at which the modified pass-through audio sounds are combined with the feedback anti-noise sounds to be selectable between at least a first location along the feedback ANR pathway where the feedback ANR and pass-through audio pathways are able to be combined and a second location along the feedback ANR pathway where the feedback ANR and pass-through audio pathways are able to be combined.

11. The ANR circuit of claim 10, wherein the feedback ANR pathway comprises a first plurality of filters operable as a first block of filters to at least generate the feedback anti-noise sounds from digital data representing the feedback reference signal, wherein the first location along the feedback ANR pathway precedes an input to the first plurality of filters, and wherein the second location along the feedback ANR pathway follows an output of the first plurality of filters.

12. The ANR circuit of claim 11, wherein the pass-through audio pathway comprises a second plurality of filters operable as a second block of filters to at least split the modified pass-through audio sounds into higher frequency sounds and lower frequency sounds at a selectable crossover frequency, and further operable to route the lower frequency sounds to the first location and the higher frequency sounds to the second location, wherein the selectable crossover frequency may be selected to route the entirety of the modified pass-through audio sounds to one or the other of the first and second locations.

13. An ANR circuit comprising:

a signal processing topology having a feedback ANR pathway, a feedforward ANR pathway, and a pass-through audio pathway, wherein the ANR circuit is structured to:

receive a feedback reference signal from a feedback microphone;

generate feedback anti-noise sounds in the feedback ANR pathway from digital data representing at least the feedback reference signal;

receive a feedforward reference signal from a feedforward microphone;

generate feedforward anti-noise sounds in the feedforward ANR pathway from digital data representing at least the feedforward reference signal;

receive a pass-through audio signal from an audio source;

generate modified pass-through audio sounds in the pass-through audio pathway from digital data representing the pass-through audio signal;

combine the feedback anti-noise sounds from the feedback ANR pathway, the feedforward anti-noise sounds from the feedforward ANR pathway, and the modified pass-through audio sounds from the pass-through audio pathway; and output an output signal conveying a combination of the feedback anti-noise sounds, the feedforward anti-noise sounds and the modified pass-through audio sounds to be acoustically output by an acoustic driver;

a compression controller monitoring the output signal; and a first VGA operable by the compression controller to reduce an amplitude of at least the feedback anti-noise sounds in response to the compression controller detecting an indication of impending clipping in the first output signal.

14. The ANR circuit of claim 13, wherein the ANR circuit is further structured to enable a point at which the modified pass-through audio sounds are combined with the feedback anti-noise sounds to be selectable between a first location along the feedback ANR pathway that precedes an input of the first VGA that enables an amplitude of the modified pass-through audio sounds to be reduced by the first VGA along with the amplitude of the feedback anti-noise sounds, and a second location along the feedback ANR pathway that follows an output of the first VGA such that the amplitude of the modified pass-through audio sounds cannot be reduced by the first VGA.

15. The ANR circuit of claim 13, further comprising a second VGA operable by the compression controller to reduce an amplitude of at least the feedforward anti-noise sounds in response to the compression controller detecting an occurrence of clipping in the first output signal.

16. An ANR circuit comprising:

a signal processing topology having a feedback ANR pathway, a feedforward ANR pathway, and a pass-through audio pathway, wherein the ANR circuit is structured to:

receive a feedback reference signal from a feedback microphone;

generate feedback anti-noise sounds in the feedback ANR pathway from digital data representing at least the feedback reference signal;

receive a feedforward reference signal from a feedforward microphone;

generate feedforward anti-noise sounds in the feedforward ANR pathway from digital data representing at least the feedforward reference signal;

receive a pass-through audio signal from an audio source;

generate modified pass-through audio sounds in the pass-through audio pathway from digital data representing the pass-through audio signal;

combine the feedback anti-noise sounds from the feedback ANR pathway, the feedforward anti-noise sounds from the feedforward ANR pathway, and the modified pass-through audio sounds from the pass-through audio pathway; and output an output signal conveying a combination of the feedback anti-noise sounds, the feedforward anti-noise sounds and the modified pass-through audio sounds to be acoustically output by an acoustic driver;

a compression controller monitoring the output signal;

a first VGA operable by the compression controller to reduce an amplitude of feedback reference sounds represented by the feedback reference signal in response to the compression controller detecting an indication of impending clipping in the first output signal; and a second VGA operable by the compression controller to reduce an amplitude of feedforward reference sounds represented by the feedforward reference signal in response to the compression controller detecting an indication of impending clipping in the first output signal.

* * * * *